United States Patent [19]

Ciganek

[11] 4,260,761
[45] Apr. 7, 1981

[54] INTERMEDIATES FOR THE PREPARATION OF OCTAHYDRO-1H-BENZO[4,5]FURO[3,2,-e]-ISOQUINOLINE ANALGESIC AND NARCOTIC ANTAGONISTIC COMPOUNDS

[75] Inventor: Engelbert Ciganek, Kennett Square, Pa.

[73] Assignee: E. I. Du Pont de Nemours and Company, Wilmington, Del.

[21] Appl. No.: 151,241

[22] Filed: May 19, 1980

Related U.S. Application Data

[60] Division of Ser. No. 54,447, Jul. 9, 1979, which is a continuation-in-part of Ser. No. 948,038, Oct. 2, 1978, abandoned.

[51] Int. Cl.$^3$ .................. C07D 217/04; A61K 31/47
[52] U.S. Cl. ...................... 546/66; 424/258
[58] Field of Search ........................... 546/66

[56] References Cited

U.S. PATENT DOCUMENTS

| | | | |
|---|---|---|---|
| 3,798,031 | 3/1974 | Janssens et al. | 96/1.8 |
| 3,830,647 | 8/1974 | Janssens et al. | 96/1.5 |
| 3,928,686 | 12/1975 | Poot et al. | 428/457 |
| 3,979,394 | 9/1976 | Janssens et al. | 260/283 BZ |

OTHER PUBLICATIONS

A. Schultz et al., J.C.S. Chem. Comm., 1976, p. 925.
A. Schultz et al., J.A.C.S., 100:7, Mar. 1978, 2150–2162.

*Primary Examiner*—Donald G. Daus
*Assistant Examiner*—M. C. Eakin

[57] ABSTRACT

Octahydro-1H-benzo[4,5]furo[3,2-e]isoquinoline compounds and processes for their manufacture are provided. The compounds correspond to the formula

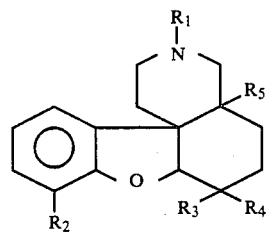

These compounds exhibit both analgesic and narcotic antagonistic properties, as well as low abuse liability.

Novel intermediate compounds are also provided which have the formula

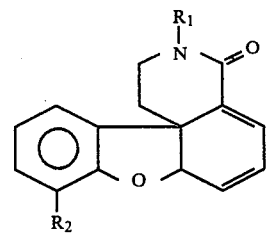

5 Claims, No Drawings

INTERMEDIATES FOR THE PREPARATION OF OCTAHYDRO-1H-BENZO[4,5]FURO[3,2,-e]-ISOQUINOLINE ANALGESIC AND NARCOTIC ANTAGONISTIC COMPOUNDS

CROSS REFERENCE TO RELATED APPLICATIONS

This is a division of application Ser. No. 54,447, filed July 9, 1979, which in turn is a continuation-in-part of copending application Ser. No. 948,038, filed Oct. 2, 1978, now abandoned.

DESCRIPTION OF THE INVENTION

1. Field of the Invention

This invention relates to novel isoquinoline analgesic and narcotic antagonistic compounds, processes for their manufacture, their use in the treatment of pain, and novel cyclohexadiene lactams as intermediates.

2. Background of the Invention

Pain is an essential sensation in the protection of the body from damaging influences. However, because said pain frequently persists after it has played its essential role, it becomes desirable to treat the subject to reduce the sensation of pain. Drugs which are effective to reduce pain, i.e., analgesics, act by different mechanisms:

(1) Drugs which reduce pain by treating its source, e.g. glyceryl trinitrate in the treatment of angina;

(2) Drugs of the non-narcotic, non-steroidal, antiinflammatory, antipyretic type, which may act in part peripherally to relieve pain by inhibition of prostaglandin synthetase, or an antiinflammatory effect, e.g. aspirin or acetaminophen; and (3) Drugs which act mainly on the perception of pain by the brain, e.g. morphine and certain morphine derivatives.

Analgesics are also classified by their mode of use. Thus, in general, when the intensity of pain is mild to moderate, a simple (mild) analgesic is given. However, when the pain is moderate to severe, a strong analgesic is indicated.

The most important strong analgesic compounds include opium preparations, purified alkaloids (morphine), semi-synthetic morphine modifications (oxymorphone) and various synthetic morphine-like compounds (phenyl piperidino structures). In addition to morphine itself, the most widely-used analgesics are oxycodone, oxymorphone, levorphanol, methadone and pethidine (meperidine). Morphine is the standard by which strong analgesics are compared.

Morphine, which acts on the central nervous system to repress pain perception, causes drowsiness, euphoria (and sometimes disphoria) and depresses respiration. Morphine and the many drugs related thereto incur high degrees of dependence. This is, of course, no problem in short-term treatment of pain, but becomes a serious problem in the treatment of chronic pain.

Because the narcotic-like analgesics also act to depress the respiratory system, over dosage of such compounds is extremely dangerous. It has been found, however, that several N-allyl derivatives, including the N-allyl derivative of morphine (nalorphine), levorphanol (levallorphan) and oxymorphone (naloxone) effectively antagonize overdoses of the opiate analgesics. Two of these, nalorphine and levallorphan, have some analgesic effects by themselves, but naloxone is a pure antagonist having no intrinsic analgesic activity. Naloxone is a versatile material which is capable of reversing the action (including the analgesia) of larger doses of a narcotic and also antagonizes the emetic effect of meperidine. Though such antagonists have been shown to be effective in antagonizing overdoses of narcotics, they have not been shown to be effective in administration with narcotics to reverse respiratory depression without also reversing the desirable analgesic effects of the opiate. Thus, it would be highly desirable to obtain a compound which combines significant narcotic analgesic activity as well as narcotic antagonistic activity into the same molecule.

Since Lasagna and Beecher (Lasagna, L. and Beecher, H. K.: The Analgesic Effectiveness of Nalorphine and Nalorphine-Morphine Combinations in Man. *J. Pharmacol. Exp. Ther.*, 112: 356–363, 1954.) reported that the narcotic antagonist nalorphine also has analgetic properties in man, a wide-ranging search for agonist/antagonist compounds possessing both analgetic and narcotic antagonist properties has led to the discovery of a number of clinically useful agents (pentazocine, cyclazocine, nalbuphine, etc.) having a lower abuse potential than pure narcotic agonist compounds. Generally (but with some exceptions), substitution of $C_2$ to $C_n$ homologs for the N-methyl group in morphine, codeine, and other narcotics produces compounds possessing an antagonist component with or without loss of analgetic potency; thus within a single chemical series there may be compounds possessing pure agonist, combined agonist/antagonist, and pure antagonist properties (Jaffe, J. H. and Martin, W. R.: Narcotic Analgesics and Antagonists, in The Pharmacological Basis of Therapeutics, L. S. Goodman and A. Gilman (eds), Macmillan Publishing Co., Inc., New York, p. 272, 1975.)

U.S. Pat. No. 3,015,661 to Georgian is directed to decahydroisoquinoline derivatives such as those corresponding to the structure

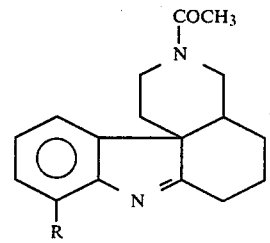

Examples of such compounds are 3-acetyl-1,2,3,4,4a-5,6,7-octahydropyrido[3,4-d]-4aH-isocarbazole and the corresponding 9-methoxy analog. This class of compounds is disclosed to be useful as intermediates for the preparation of natural alkaloids and hydrocarbazolenines.

More clearly of interest is the work of Schultz et al., which is directed to the preparation of morphine—Schultz, A. G. and Lucci, R. D., *J. C. S. Chem. Comm.*, 925 (1976); and Schultz, A. G., Lucci, R. D., Fu, W. Y., Berger, M. H., Erhardt, S., and Hagmann, W. K., *J. Am. Chem. Soc.*, 100, 2150 (1978). Both of the papers by Schultz et al. describe the following reaction:

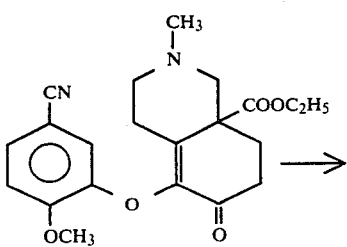

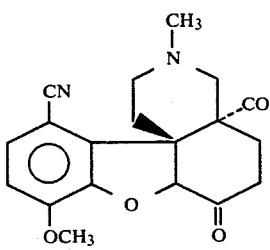

The compound having a cis-fused dihydrofuran structure is disclosed to be useful as an intermediate for the synthesis of morphine alkaloids in that it has the functionality necessary for formation of the remaining carbon-carbon bond in the morphine alkaloids.

SUMMARY OF THE INVENTION

The invention is primarily directed to a novel class of octahydro-1H-benzo[4,5]furo[3,2-e]isoquinoline compounds corresponding to the following formula:

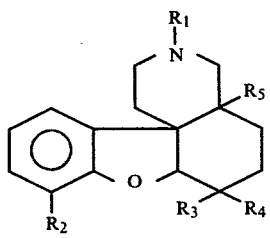

wherein
$R_1$ is selected from the group consisting of —H, $C_{1-10}$ alkyl, —$CH_2$—$R_6$,

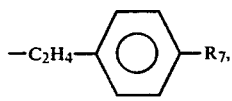

and $(CH_2)_nCN$ in which n=1–3;
$R_2$ is selected from the group consisting of —H, —OH, $C_{1-2}$ alkoxy and $C_{2-12}$ acyloxy of an alkanoic acid;
$R_3$ is separately selected from the group consisting of —H, —OH, —$CH_3$, $C_{1-2}$ alkoxy, $C_{2-12}$ acyloxy of an alkanoic acid, —F and —$N_3$;
$R_4$ is separately selected from the group consisting of —H and —F;
$R_{3-4}$ in combination are selected from the group consisting of methylene and keto;
$R_5$ is selected from the group consisting of —H, —OH,

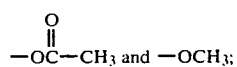

and —$OCH_3$;
$R_6$ is selected from the group consisting of

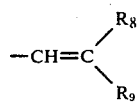

—C≡CH, $C_{3-6}$ cycloalkyl, 2-thienyl, 2-furyl and 2-tetrahydrofuryl, the 2-furyl and 2-tetrahydrofuryl optionally substituted with a methyl group;
$R_7$ is selected from the group consisting of $C_{1-3}$ alkyl, —$OCH_3$, —Cl, —Br and —F; and
$R_8$ and $R_9$ are independently selected from the group consisting of —H, —$CH_3$ and —Cl; and
pharmaceutically suitable acid addition salts thereof.

The invention is also directed to pharmaceutical compositions containing the above-described compounds and to the method of using them for the treatment of pain and to antagonize the effects of narcotics. In another aspect of the invention, it is directed to novel intermediate compounds which are useful to make the primary compounds and to the method of making those intermediates.

DETAILED DESCRIPTION OF THE INVENTION

Within the context of the general formula of the octahydro-1H-benzo[4,5]furo[3,2-e]isoquinolines of the invention given hereinabove, it has been found that certain structural variations are preferred because of the indication of greater analgesic and/or narcotic antagonistic effectiveness.

The preferred compounds of the invention are those in which independently (a) $R_1$ is $C_{1-6}$ alkyl or cyclopropylmethyl, of which cyclopropylmethyl and $C_{1-4}$ alkyl are most preferred;

(b) $R_2$ is —OH or —$OCH_3$, of which —OH is most preferred;

(c) $R_3$ and $R_4$ are both —H; $R_3$ is —OH and $R_4$ is —H; $R_3$ and $R_4$ are both —F; and $R_3$ and $R_4$ together form a keto group, most preferred of which is when $R_3$ and $R_4$ are both —H;

(d) $R_5$ is —H or —OH of which —H is most preferred.

The most preferred compound is 3-cyclopropylmethyl-1,2,4,4a$\alpha$,5,6,7,7a$\alpha$-octahydro-1H-benzo[4,5-]furo[3,2-e]-isoquinolin-9-ol.

GENERAL REACTION SEQUENCE

The compounds of the invention are synthesized by the following general sequence of reactions:

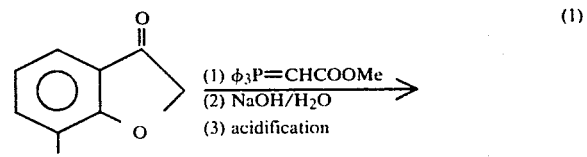

(1)

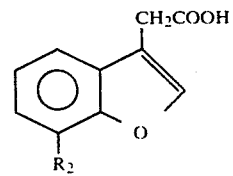

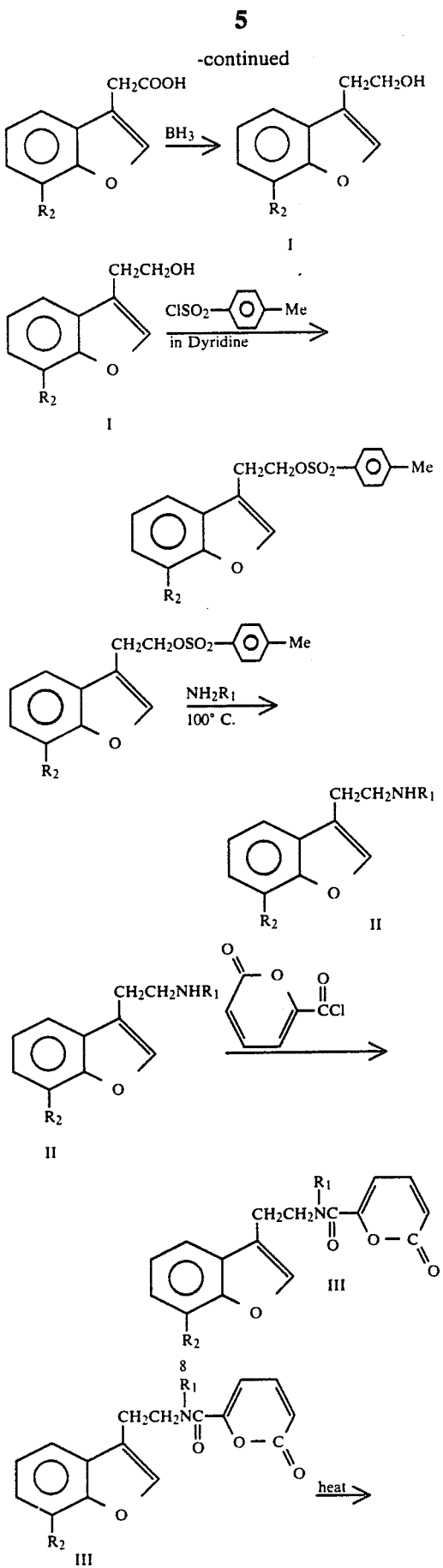
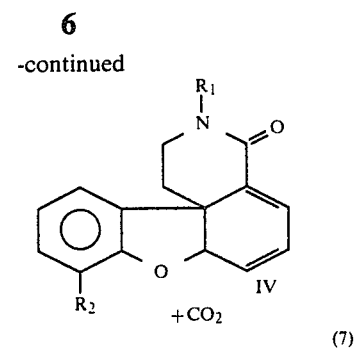

PROCESS CONDITIONS (1) Wittig Reaction

This first reaction of the process sequence is conducted in a non-aqueous system in the liquid phase at a temperature of 80°–160° C. A temperature of at least about 110° C. is preferred in order to get a satisfactorily fast rate of reaction. A slight excess of the phosphorane reactant is utilized to drive the reaction to completion. Upon completion of the reaction, the system is boiled with strong base to convert the ester of the acid salt, which mixture is then extracted with methylene chloride to remove the triphenylphosphine oxide. The resultant water layer is acidified to convert the salt to the acid.

(2) Metal Hydride Reduction

The acidic product of the Wittig reaction can be reduced to the alcohol (I) by reduction with any complexed metal hydride, such as LiAlH₄ or with BH₃.(CH₃)₂S or BH₃.tetrahydrofuran. The highly exothermic reaction is conducted as a non-aqueous system in the liquid phase at a temperature of 0°–30° C. Borane is preferred in the complex because it is both inexpensive and easy to handle safely. It is preferred to use a slight excess of reagent complex in order to assure complete reaction. The reduced product can be easily recovered by extracting the reaction product with methylene chloride and distilling off the solvent from the extract under a high vacuum.

(3) Reaction with p-toluenesulfonyl chloride

This reaction is carried out at low temperature (0°–30° C.) to avoid decomposition of the reaction product, using as solvent for the system a basic compound which will also remove byproduct HCl as it is formed. Suitable solvents include pyridine, substituted pyridines, isoquinoline and the like. The reaction sometimes is completed in a few minutes but may require several days when kept in a refrigerator.

(4) Amine Substitution

Using crude product from reaction (3), a large excess of alkylamine (R₁NH₂) is added to avoid the formation of tertiary amine byproducts and other side reactions. The reaction is carried out under pressure to contain the reaction at a temperature of 50°–150° C. In general, the reaction time is reduced by operating at the higher temperatures.

(5) Amide Preparation

The amine reaction product of step (4) is converted to the desired α-pyronecarboxamide by reaction at 0°–30° C. in the liquid phase with the reaction product of a mixture of either 3- or 6-α-pyronecarboxylic acid and thionyl chloride, in an inert solvent system. Suitable solvents are non-alcoholic solvents, such as tetrahydrofuran, toluene and methylene chloride. Pyridine is also used in the reaction system to render the system basic and to take up HCl as it is formed and avoid the consumption of amine starting material. It is preferred to use a slight excess of the pyrone acid chloride to obtain a more favorable reaction rate. Unreacted pyrone acid chloride reactant is removed from the reaction product by base extraction.

(6) Intramolecular Diels-Alder Reaction

This novel reaction step is carried out by maintaining the α-pyronecarboxamide reaction product of step (5) at a temperature of 150°–500° C. for a time sufficient to obtain substantial Diels-Alder reaction without incurring thermal degradation of either the reactant or the resultant reaction product. Thus, shorter reaction times must be used at higher temperatures to avoid such decomposition. The reaction can be carried out in either the liquid or vapor phase. When carried out in the liquid phase, the reactant is preferably dissolved in an inert solvent, such as aromatic hydrocarbons, chlorinated aromatic hydrocarbons and aliphatic or aromatic ethers. At preferred reaction temperatures of 150°–300° C., the liquid phase reaction can be carried out in as little as about one minute or over the course of several weeks. To avoid yield loss due to polymerization of the reactant, the reaction may be carried out in an evacuated steel or glass vessel after the reactant and/or reactant solution has been thoroughly degassed. Undesirable polymerization of the reactant can also be reduced by the presence of a free radical polymerization inhibitor, such as phenothiazine. It is preferred to carry out the reaction by refluxing a dilute (about 0.5–1% by weight) solution in 1,2,4-trichlorobenzene under nitrogen for a time sufficient to obtain substantial Diels-Alder product. The reaction time for this preferred method depends on the nature of the substituent R₁. The reaction can also be carried out by distilling the reactant at a temperature of 300°–500° C. under vacuum through a heat exchange medium such as a hot quartz tube packed with quartz chips.

(7) Reduction of Cyclohexadiene Ring

The cyclohexadiene ring of the reaction product of step (6) is reduced to saturation by conventional catalytic hydrogenation in the liquid phase at 20°–100° C. Conventional hydrogenation catalysts can be used such as Raney nickel, platinum, palladium, any of which can be supported on suitable carriers. The reaction is carried out with an excess of hydrogen and at comparatively mild conditions of temperature and pressure in order to reduce only the hexadiene ring and to avoid reduction of the benzene ring.

(8) Reduction of Lactam to Amine

Like reaction (2), reduction of the lactam intermediate product to the amine involves use of a complex metal hydride, such as LiAlH₄ or with BH₃. (CH₃)₂S or BH₃.tetrahydrofuran. To obtain a satisfactorily rapid reaction rate, the reaction should be carried out in the liquid phase at a temperature of at least about 50° C. A preferred method of carrying out the reaction is with solvent reflux. Thus, the reaction is effected at essentially the boiling point of the solvent. When a metal hydride complex, such as BH₃/tetrahydrofuran/methyl sulfide is used, the complex is decomposed upon completion of the reaction by heating the reaction system with acid, preferably an organic acid such as acetic acid.

In one variation of the above-described reaction sequence, which is useful when R₁ is hydrogen, by replacing the carbomethoxymethylenetriphenylphosphorane with cyanomethylenetriphenylphosphorane, the reaction product of step (1) can be reduced directly with LiAlH₄ to reaction product (II), thus avoiding reactions (3) and (4). The amine (II, R₁=H) can be converted to a secondary amine by alkylation or acylation followed by reduction (see Example 4b):

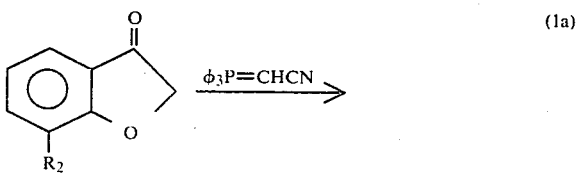

(1a)

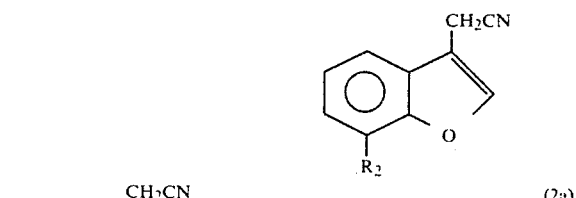

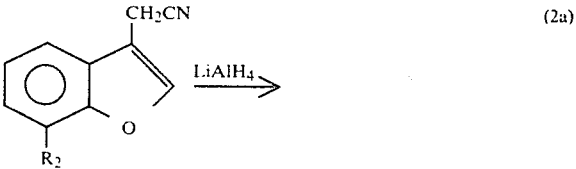

(2a)

-continued

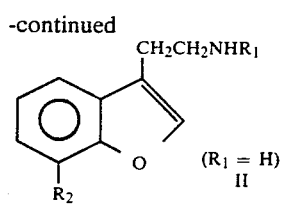

(R₁ = H)
II

The following table shows representative compounds readily available by the above processes and whose specific description follows.

| R₁ | R₂ | R₃ | R₄ | R₅ |
|---|---|---|---|---|
| —CH₃ | —H | —H | —H | —H |
| —CH₃ | —OCH₃ | —H | —H | —H |
| —CH₃ | —OH | —H | —H | —H |
| —CH—▷ | —OCH₃ | —H | —H | —H |
| —CH₂—▷ | —OH | —H | —H | —H |
| —CH₂—☐ | —OCH₃ | —H | —H | —H |
| —CH₂—☐ | —OH | —H | —H | —H |
| —CH₂CH₂CH₃ | —OH | —H | —H | —H |
| —CH₂CH₂—⟨O⟩—CH₃ | —OH | —H | —H | —H |
| —CH₂—⟨O⟩ (tetrahydropyran) | —OCH₃ | —H | —H | —H |
| —CH₂CH₂—⟨O⟩—Cl | —OH | —H | —H | —H |
| —CH₂—⟨cyclohexyl⟩ | —OC₂H₅ | —H | —H | —H |
| —H | —OCH₃ | —H | —H | —H |
| —H | —OC₂H₅ | —H | —H | —H |
| —CH₂CH=CH₂ | —OCH₃ | —H | —H | —H |
| —CH₂—⟨S⟩ | —OCH₃ | —H | —H | —H |
| —CH₂—⟨O⟩ | —OCH₃ | —H | —H | —H |
| —CH₂CH₂CN | —OCH₃ | —H | —H | —H |
| —CH₃ | —OC₂H₅ | —H | —H | —H |
| —CH₂—▷ | —OCOC₃H₇ | —H | —H | —H |
| —CH₂—▷ | —OCH₃ | —OH | —H | —H |
| —CH₂—▷ | —OCH₃ | —OCOCH₇ | —H | —H |
| —CH₂—▷ | —OCH₃ | —F | —H | —H |
| —CH₂—▷ | —OCH₃ | —N₃ | —H | —H |
| —CH₂—▷ | —OCH₃ | R₃ + R₄ = O | | —H |
| —CH₂—▷ | —OCH₃ | —CH₃ | —H | —H |

-continued

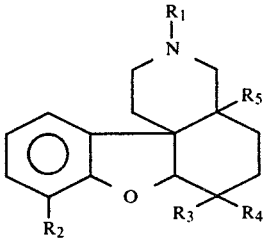

| R₁ | R₂ | R₃ | R₄ | R₅ |
|---|---|---|---|---|
| —CH₂—△ | —OCH₃ | —F | —F | —H |
| —CH₂—△ | —OCH₃ | —OH | —H | —OH |
| —CH₂—△ | —OCH₃ | —H | —H | —OH |
| —(CH₂)₅CH₃ | —OCOCH₃ | —H | —H | —OCOCH₃ |
| —CH(CH₃)CH₂CH₃ | —OCO(CH₂)₁₀CH₃ | —H | —H | —H |
| —CH₂CN | —OCH₃ | —H | —H | —H |
| —(CH₂)₃CN | —OCH₃ | —H | —H | —H |
|  | —OCH₃ | —H | —H | —H |
| —CH₂CH₂—⟨O⟩—CH(CH₃)₂ | —OCH₃ | —H | —H | —H |
| —CH₂CH₂—⟨O⟩—F | —OCH₃ | —H | —H | —H |
| —CH₂CH=C(CH₃)₂ | —OCH₃ | —H | —H | —H |
| —CH₂CH=CCl₂ | —OCH₃ | —H | —H | —H |
| —CH₂CH=CHCH₃ | —OCH₃ | —H | —H | —H |
| —CH₂—C≡CH | —OCH₃ | —H | —H | —H |
|  | —OCH₃ | —OCH₃ | —H | —OCH₃ |
| —CH₂—□ | —OCH₃ | —OC₂H₅ | —H | —H |
| —CH₂—□ | —OCH₃ | —OCO(CH₂)₁₀CH₃ | —H | —H |
| —CH₂—□ | —OCH₃ | R₃ + R₄ = CH₂ | | —H |
| —CH₂—△ | | | | |

The compounds of the invention, their use and the process for making them will be better understood by reference to the following examples, in which all indications of percentage are by weight unless indicated otherwise and temperatures are in degrees Celsius. The compounds of the examples have the trans rather than the cis configuration, corresponding to that determined for the product of Example 5.

In these molecules d and l optical isomers occur as racemic mixtures which can be resolved by known methods (Eliel, *Stereochemistry of Carbon Compounds*, McGraw-Hill, 1962, p. 21). The optical isomers corresponding to the absolute configuration of morphine are more active and preferred. Similarly, where compounds carry a 7-hydroxyl group, the β-isomers, having the same stereochemistry relative to the furan ring as in morphine, are preferred.

EXAMPLES

EXAMPLE 1

3-Methyl-2,3,4,4aα,5,6,7,7aα,-octahydro-1H-benzo[4,5-]furo-[3,2-e]isoquinoline (VI, R₁=Me; R₂=H)

(a) 3-Benzofuranethanol (I; R₂=H)

A mixture of 71.1 g of 3-benzofuranone [D. C. Schroeder, P. O. Corcoran, C. A. Holden, and M. C. Mulligan, *J. Org. Chem.*, 27, 586 (1962)], 210 g of carbomethoxymethylenetriphenylphosphorane and 300 ml of toluene was heated under reflux for 8 hours. The solvent was removed and the residue stirred with ether and filtered. The filtrate was concentrated and the residue heated under reflux with 300 ml of methanol and 300 ml of 15% sodium hydroxide solution for 2 hours. The cooled mixture was diluted with water and extracted several times with methylene chloride. Acidification of the water layer and extraction with methylene chloride gave 88.3 g of crude 3-benzofuranacetic acid. The product was dissolved in 500 ml of tetrahydrofuran, and 50 g of borane-methyl sulfide complex added. After stirring at room temperature overnight, the excess reagent was destroyed by slow addition of 100 ml of conc. hydrochloric acid. The mixture was made basic and extracted several times with methylene chloride and the product shortpath distilled (bath temperature) 110°, 1 micron pressure) to give 65.8 g (76%) of 3-benzofuranethanol. NMR spectrum (in CDCl₃): τ2.3–3.0 (m, 5); 6.2 (t, J=6 Hz, 2) 7.1 (t, J=6 Hz, 2) and 7.3 (s, 1).

(b) N-Methyl-3-benzofuranethylamine (II, R₁=Me, R₂=H)

A solution of 5.03 g of 3-benzofuranethanol and 8 g of p-toluenesulfonyl chloride in 20 ml of pyridine was kept in a refrigerator for one week. Most of the pyridine was removed under vacuum, and the residue dissolved in ether and washed successively with 5% hydrochloric acid, water, and 5% sodium bicarbonate solution and dried. Removal of the solvent left 5.93 g of crude 3-benzofuranethanol, p-toluenesulfonate which was heated with 8 g of methylamine in 25 ml of tetrahydrofuran to 100° for 4 hours. The mixture was concentrated, made basic with aqueous sodium hydroxide, and extracted with methylene chloride. The crude amine so obtained was short-path distilled (bath 120°, 0.5 micron) to give 3.17 g (59% yield) of N-methyl 3-benzofuranethylamine. NMR spectrum (in CDCl$_3$): τ2.4–3.0 (m, 5); 7.2 (s, 4); 7.6 (s, 3) and 9.0 (s, 1).

(c)
N-(3-Benzofuranethyl)-N-methyl-6-α-pyronecarboxamide (III, R$_1$=Me; R$_2$=H)

A mixture of 1.05 g of 6-α-pyronecarboxylic acid [R. H. Wiley and A. J. Hart, *J. Am. Chem. Soc.*, 76, 1942 (1954)], 7 ml of thionyl chloride and one drop of dimethylformamide was heated under reflux for twenty minutes. The excess reagent was removed under vacuum, the residue dissolved in toluene, and the solvent removed under vacuum. The residue (6-pyronecarbonyl chloride) was dissolved in 3 ml of methylene chloride and the solution added slowly to a stirred mixture of 1.34 g of N-methyl-3-benzofuranethylamine, 2 ml of pyridine, and 3 ml of methylene chloride, keeping the temperature below 20°. The mixture was stirred at room temperature for one hour, toluene added, and the toluene solution successively washed with 10% hydrochloric acid, water, and 5% sodium bicarbonate solution. Removal of the solvent gave 2.04 g (91% yield) of III (R$_1$=Me; R$_2$=H); nmr spectrum (in CDCl$_3$): τ2.2–4.0 (m, 8); 6.3 (t, J=7 Hz, split further, 2); 7.0 (s, 3), and 7.1 (t, J=7 Hz, split further, 2).

(d)
3-Methyl-2,3-dihydro-1H-benzo[4,5]furo[3,2-e]-isoquinolin-4[7aH]-one (IV; R$_1$=Me; R$_2$=H).

A deoxygenated solution of 1.72 g of III (R$_1$=Me, R$_2$=H) in 50 ml of toluene, contained in an evacuated sealed glass tube, was heated to 225° for 8 hours. Removal of the solvent and crystallization of the residue from toluene gave 0.66 g of IV (R$_1$=Me; R$_2$=H) containing ca. 20% impurities (part of which is toluene). 220 MHz nmr spectrum (in CDCl$_3$): τ2.5–3.5 (m+d, J=6 Hz, 5); 4.0 (d/d/d,J=10/6/2/ Hz, 1); 4.2 (d/d, J=10/3 Hz, 1); 4.6 (narrow t, J~2 Hz, 1); 6.5 (t/d, J=13/4 Hz, 1); 6.8 (d/d/d, J=13/6/2 Hz, 1); 6.9 (s, 3); 7.8 (t/d, J=13/6 Hz, 1) and 8.1 (d/d, J=13/4/2 Hz, 1).

(e)
3-Methyl-2,3,5,6,7,7aα-hexahydro-1H-benzo[4,5]furo-[3,2-e]isoquinolin-4[4aαH]-one (V; R$_1$=Me; R$_2$=H)

A solution of 0.76 g of IV (R$^1$=Me; R$^2$=H) in tetrahydrofuran was stirred under hydrogen in the presence of a palladium-on-charcoal catalyst until saturation of the two double bonds was complete. Removal of the solvent from the filtered mixture gave 0.72 g of V (R$_1$=Me; R$_2$=H) of ca. 90% purity; 220 MHz nmr spectrum (in CDCl$_3$): τ2.8–3.3 (m, 4); 5.6 (d/d, J=8/6 Hz, 1); 7.1 (s, 3) and 6.5–8.9 (m, 11).

(f)
3-Methyl-2,3,4,4aα,5,6,7,7aα-octahydro-1H-benzo[4,5-]furo[3,2-e]isoquinoline (VI, R$_1$=Me, R$_2$=H)

A mixture of 0.72 g of crude V (R$_1$=Me; R$_2$=H), 7 ml of tetrahydrofuran and 0.7 ml boranemethyl sulfide complex was heated under reflux overnight. Excess borane was destroyed by slow addition of conc. hydrochloric acid to the cooled mixture which was then made basic and extracted with methylene chloride. The product obtained on removal of the solvent was heated under reflux with 5 ml of acetic acid for 5 hours. The product was partitioned into neutral and basic fractions with toluene and dilute hydrochloric acid and the basic fraction, recovered from the acid solution with sodium hydroxide and methylene chloride, sublimed (0.5 micron, 120°–140° bath temperature) to give 0.24 g of VI (R$_1$=Me; R$_2$=H); 220 MHz nmr spectrum (in CDCl$_3$): τ2.6 (d/d, J=8/2 Hz, 1); 2.9 (t/d, 8/2 Hz, 1); 3.2 (m, 2); 5.7 (skewed triplet, J≈5 Hz); 7.7 (s, 3) and 7–9 (m, 13).

EXAMPLE 2

9-Methoxy-3-methyl-2,3,4,4aα-5,6,7,7aα-octahydro-1H-benzo[4,5]furo[3,2-e]isoquinoline (VI; R$_1$=Me; R$_2$=OMe)

(a) 7-Methoxy-3-benzofuranethanol (I; R$_2$=MeO)

7-Methoxy-3-benzofuranone (prepared from methyl o-vanillate according to the literature procedure cited in Example 1a) was converted to 7-methoxy-3-benzofuranethanol as described in Example Ia. The product, obtained in 79% overall yield after short-path distillation (140°–180° bath temperature, 0.5 micron pressure), had the following nmr spectrum (in CDCl$_3$): 2.7 (narrow m, 1); 3.1–3.6 (m, 3); 6.2–6.6 (s+t, J=6.5 Hz, +broad s, 6) and 7.4 (t, J=6.5 Hz, 2).

(b) 7-Methoxy-N-methyl-3-benzofuranethylamine (II, R$_1$=Me; R$_2$=MeO) was obtained in 75% overall yield from 7-methoxy-3-benzofuranethanol as described in Example 1b; nmr spectrum (in CDCl$_3$): τ2.3 (narrow m, 1); 2.5–3.1 (m, 3); 5.8 (s, 3); 6.9 (narrow m, 4); 7.3 (s, 3) and 8.0 (s, 1).

(c)
9-Methoxy-3-methyl-2,3-dihydro-1H-benzo[4;5]-furo[3,2-e]isoquinolin-4[7aH]-one (IV, R$_1$=Me; R$_2$-MeO)

7-Methoxy-N-methyl-3-benzofuranethylamine was treated with 6-α-pyronecarbonyl chloride as described in Example 1c and the resulting N-(9-methoxy-3-benzofuranethyl), N-methyl-6-α-pyronecarboxamide (III, R$^1$=Me, R$^2$=MeO) heated in toluene solution to 215° for 12 hours as described in Example 1d. Crystallization from toluene gave IV (R$_1$=Me; R$_2$=MeO) in 20% overall yield, mp 175°–176° after drying at 110°/1 micron. 220 MHz nmr spectrum (in CDCl$_3$): τ3.1 (d, J=6 Hz, 1); 3.3–3.5 (m, 2); 3.6 (d/d, J=6.5/2.5 Hz, 1); 4.1 (d/d/d; J=10/6/2 Hz, 1); 4.3 (d/d/, J=10/2 Hz, 1); 4.7 (narrow m, 1); 6.3 (s, 3); 6.6 (t/d, J=12.5/4 Hz, 1); 6.9 (d/d/d; J=12.5/6/2 Hz, 1); 7.7 (s, 3); 8.0 (t/d, J=12.5/6 Hz, 1); and 8.3 (d/d/d/; J=12.5/4/2 Hz).

Anal. Calcd. for C$_{17}$H$_{17}$NO$_3$: C, 72.06; H, 6.05; N, 4.94; Found: C, 71.60; H, 5.98; N, 4.90.

(d)
9-Methoxy-3-methyl-2,3,4,4aα,5,6,7,7aα-octahydro-1H-benzo[4,5]furo[3,2-e]isoquinoline (VI, R₁=Me; R₂=MeO)

Following the procedure of Example 1, 9-methoxy-3-methyl-2,3,5,6,7,7aα-hexahydro-1H-benzo[4,5]furo[3,2-e]isoquinolin-4[4αH]-one (VI, R₁=Me; R₂=MeO) was obtained by catalytic hydrogenation of IV (R¹=Me; R²=MeO); 220 MHz nmr spectrum (in CDCl₃): 2.9–3.1 (m, 2); 3.2–3.4 (m, 1); 5.3 (d/d, J=8/6 Hz, 1); 5.9 (s, 3); 6.8 (s, 3) and 6.4–8.7 (m, 11); the spectrum also indicated the presence of ca. 10% of an impurity. Reduction with borane-methyl sulfide as described in Example 1f gave VI (R₁=Me, R₂=MeO) in 69% overall yield after sublimation (160° bath temperature, 0.5 micron pressure), mp 63°–64°. Mass spectrum: m/e calcd. 273.1728; found: 273.1716. 220 MHz nmr spectrum (in CDCl₃): τ2.9 (m, 1); 3.3 (m, 2); 5.6 (t, J=5.5 Hz, 1); 6.2 (s, 3); 7.6 (s, 3) and 6.2–9.0 (m, 13); the spectrum also indicated the presence of ca. 10% of an impurity.

Anal. Calcd. for C₁₇H₂₃NO₂: C, 74.69; H, 8.48; N, 5.12; Found: C, 74.79; H, 8.30; N, 5.40.

EXAMPLE 3
3-Methyl-2,3,4,4aα,5,6,7,7aα-octahydro-1H-benzo[4,5]furo[3,2-e]isoquinolin-9-ol (VI, R₁=Me; R₂=OH)

A mixture of 1.09 g of VI (R₁=OMe, R₂=Me; Example 2d) and 2.3 g of pyridine hydrochloride was stirred in an oil bath, kept at 190° for 4 hours. The cooled mixture was stirred with aqueous sodium carbonate solution and methylene chloride, the organic phase dried and the residue left after removal of the solvent crystallized from 15 ml of 95% ethanol to give 0.60 g (58% yield) of VI (R₁=Me; R₂=OH), mp 218°–220°. Mass spectrum: m/e calcd. 259.1572; found: 259.1561

Anal. Calcd. for C₁₆H₂₁NO₂: C, 74.10; H, 8.16; N, 5.40; Found: C, 74.28; H, 7.93; N, 5.63.

Addition of 8.60 g of VI (R₁=Me; R₂=H) to a boiling solution of 12.82 g of d-dibenzoyltartaric acid in 100 ml of ethanol gave, after cooling, 4.33 g of a precipitate. It was reconverted to the free base with aqueous sodium carbonate. Crystallization from 90% aqueous ethanol gave the (+) isomer of VI (R₁=Me; R₂=H), mp 163°–164°., [α]$_D$=+53.2° (C=1.01 in chloroform). The mother liquors from above were converted to the free base which was then treated with l-dibenzoyltartaric acid as described above, giving eventually the (−) isomer of VI (R₁=Me; R₂=H), mp 163°–164°, [α]$_D$=−51.9°.

EXAMPLE 4
3-Cyclopropylmethyl-9-methoxy-2,3,4,4aα,5,6,7,7aα-octahydro-1H-benzo[4,5]furo[3,2-e]isoquinoline (VI;

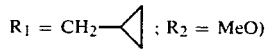

(a) 7-Methoxy-3-benzofuranethylamine (II, R₁=H, R₂=MeO)

A mixture of 26.7 g of the tosylate of 7-methoxy-3-benzofuranethanol (Example 2a), prepared as described in Example 1b, 300 ml of tetrahydrofuran and 100 g of ammonia was heated in a pressure vessel to 100° for 4 hours. The crude product was partitioned into basic and neutral fractions, and the basic fraction short-path distilled (to 170° bath temperature, 1 micron pressure) to give 11.2 g (76%) of 7-methoxy-3-benzofuranethylamine; nmr spectrum (in CDCl₃): τ2.6 (s, 1); 2.9–3.4 (m, 3); 6.1 (s, 3); 6.9–7.5 (m, 4) and 8.9 (s, 2).

(b)
N-Cyclopropylmethyl-7-methoxy-3-benzofuranethylamine

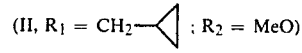

To a mixture of 10.27 g of 7-methoxy-3-benzofuranethylamine, 60 ml of methylene chloride, and 60 ml of 15% aqueous sodium hydroxide solution was added, with cooling, 8 ml of cyclopropanecarbonyl chloride. The mixture was stirred at room temperature overnight; an additional 2 ml of cyclopropanecarbonyl chloride added after two hours. The solvent was removed from the dried organic layer and the residue heated under reflux with 3.5 g of lithium aluminum hydride in tetrahydrofuran for 6 hours. Water (3.5 ml), 15% aqueous sodium hydroxide solution (3.5 ml) and finally water (10.5 ml) were added with cooling, and the mixture filtered. Removal of the solvent and short-path distillation of the residue (bath to 170°, 1 micron pressure) gave 11.74 g (90% yield) of N-cyclopropylmethyl-7-methoxy-3-benzofuranethylamine; nmr spectrum (in CDCl₃): τ2.6 (s, 1); 2.8–3.4 (m, 3); 6.1 (s, 3); 7.1–7.4 (m, 4); 7.6 (d, J=6.5 Hz, 2) and 8.1–10.2 (m, 6).

(c)
3-Cyclopropylmethyl-9-methoxy-2,3-dihydro-1H-benzo[4,5]furo[3,2-e]isoquinolin-4[7aH]-one

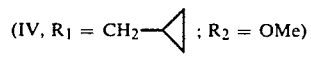

A solution of 6-α-pyronecarbonyl chloride, prepared from 43 g of the acid, in 200 ml of methylene chloride was added to a stirred mixture of 71.1 g of N-cyclopropylmethyl-7-methoxy-3-benzofuranethylamine, 100 ml of pyridine and 200 ml of methylene chloride, keeping the temperature below 15°. The mixture was stirred at room temperature for 1 hour, and acidified, keeping the temperature below 20°. Sufficient toluene was added to cause the organic phase to be the upper layer. The layers were separated and the aqueous phase was extracted with toluene. The combined organic phases were washed twice with water and then with 5% aqueous sodium bicarbonate solution. Removal of the solvent from the dried solution gave 104.1 g of amide III

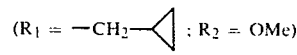

which was heated under reflux with 16 liters of 1,2,4-trichlorobenzene under nitrogen for 7 hours. Removal of the solvent and crystallization of the residue from ethyl acetate gave 45.10 g of IV

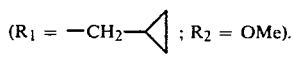

Purification of the mother liquor by high-pressure liquid chromatography (silica gel, hexane-ethyl acetate 1:1) followed by crystallization from ethyl acetate gave an additional 10.85 g of product. Combined yield: 55.95 g (59%). An analytical sample (ethyl acetate) had mp 133°–134°.

Mass spectrum: m/e calcd. 323.1521; Found: 323.1526

Anal. Calcd. for $C_{20}H_{21}NO_3$: C, 74.29; H, 6.54; N, 4.33. Found: C, 74.16; H, 6.50; N, 4.24.

(d)

3-Cyclopropylmethyl-9-methoxy-2,3,4,4aα,5,6,7,7aα-octahydro-1H-benzo[4,5]furo[3,2-e]isoquinoline

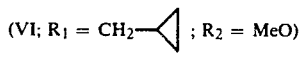

A solution of 15.21 g of IV

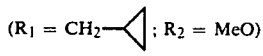

in tetrahydrofuran was shaken with 2.84 g of palladium on charcoal (10%) at 50 p.s.i. initial hydrogen pressure for 3.5 days. Removal of the solvent from the filtered solution gave crude V

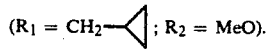

It was heated under reflux with 15 ml of borane-methyl sulfide complex in tetrahydrofuran overnight. The excess borane was destroyed by addition of conc. hydrochloric acid, and the solvent was removed. The residue was made basic with 15% aqueous sodium hydroxide solution and extracted with methylene chloride. The solvent was removed, and the residue was heated under reflux with 60 ml of acetic acid and 20 ml of conc. hydrochloric acid for two hours. The solvents were removed, and the residue was made basic. Extraction with methylene chloride, removal of the solvent from the dried extracts and short-path distillation of the residue (170° bath, 0.5 micron pressure) gave 12.65 g (86% yield) of VI

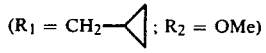

as a viscous oil. Mass spectrum: m/e calcd. 313.2040; found: 313.2045; 220 MHz nmr spectrum (in $CDCl_3$): τ2.7–3.3 (two multiplets, 1 and 2H, respectively); 5.5 (t, J=5.5 Hz, 1); 6.1 (s, 3) and 6.8–10.0 (m, 20).

EXAMPLE 5

3-Cyclopropylmethyl-2,3,4,4aα,5,6,7,7aα-octahydro-1H-benzo[4,5]furo[3,2-e]isoquinolin-9-ol

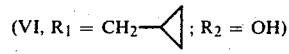

A mixture of 28.29 g of VI

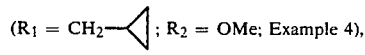

300 ml of anhydrous dimethyl formamide, 30 g of potassium t-butoxide and 35 ml of n-propyl mercaptan was stirred under nitrogen in an oil bath at 130° for 5 hours. Acetic acid (30 ml) was added slowly to the cooled mixture, which was then concentrated under vacuum. The residue was stirred with dilute hydrochloric acid and ether, and the acid layer was made basic with aqueous sodium carbonate solution and the precipitate was collected by filtration, washed with water and dried to give 25.46 g of VI,

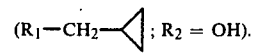

Crystallization of 19.88 g of this product (from another run) from 190 ml of 90% aqueous ethanol gave 12.47 g of pure product, m.p. 175°.

Mass spectrum: m/e calcd. 299.1885; found 299.1880; 220 MHz nmr spectrum (in $CDCl_3$): τ2.5 (broad band, OH; 1); 3.1 (d, J=6 Hz, split further, 1); 3.3 (m,2); 5.6 (t, J≃5–6 Hz, 1) and 6.6–10.0 (m, 20).

Anal. Calcd. for $C_{19}H_{25}NO_2$: C, 76.22; H, 8.42; N, 4.68; Found: C, 76.15; H, 8.38; N, 4.45.

Crystals of the compound are monoclinic, space group $P2_{1,c}$, with the following unit-cell parameters at 25° C.: a=13.384(3), b=10.083(2), c=24.324(3) Å, and β=92.84(1)°. The crystal structure, as determined by an x-ray diffraction study, consists of two independent molecules linked in chains by OH—N hydrogen bonds. The C(12a)-C(12b)-C(4a)-H torsion angles for the two molecules are 172.6° and 175.0°; the configurations about the C(12b)-C(4a) bond is thus trans with respect to the hydrogen on C(4a) and the benzene ring on C(12b).

EXAMPLE 6

3-Cyclobutylmethyl-9-methoxy-2,3,4,4aα,5,6,7,7aα-octahydro-1H-benzo[4,5]furo[3,2-e]isoquinoline

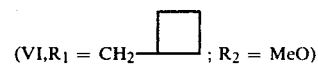

(a)
N-Cyclobutylmethyl-7-methoxy-3-benzofuranethylamine

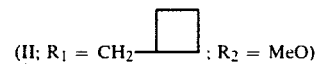

was prepared as described in Example 4b substituting cyclobutanecarbonyl chloride for cyclopropanecarbonyl chloride; nmr spectrum (in CDCl$_3$): τ2.5–3.4 (m, 4); 6.1 (s, 3) and 7.0–8.7 (m, 14).

(b) 3-Cyclobutylmethyl-9-methoxy-2,3,4,4aα,5,6,7,7aα-octahydro-1H-benzo[4,5]furo[3,2-e]isoquinoline

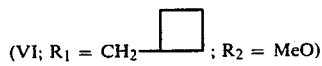
(VI; R$_1$ = CH$_2$—☐; R$_2$ = MeO)

Following the procedure of Examples 4c and 4d but omitting purification at the stage of V, 4.13 g of N-cyclobutylmethyl-7-methoxy-3-benzofuranethylamine was converted to 1.27 g (24% overall yield) of VI

(R$_1$ = CH$_2$—☐; R$_2$ = MeO)

after short-path distillation (bath to 180°, 1 micron pressure). The 220 MHz nmr spectrum was similar to that of VI

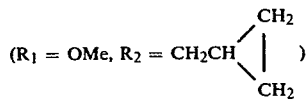
(R$_1$ = OMe, R$_2$ = CH$_2$CH$\langle$CH$_2$/CH$_2\rangle$)

except that the cyclobutyl protons occurred at lower field than the cyclopropyl protons; the spectrum indicated the presence of ca. 20% impurities. This material was used without further purification in Example 7.

EXAMPLE 7

3-Cyclobutylmethyl-2,3,4,4aα,5,6,7,7aα-octahydro-1H-benzo[4,5]furo[3,2-e]isoquinoline-9-ol

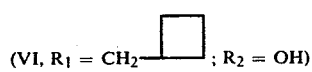
(VI, R$_1$ = CH$_2$—☐; R$_2$ = OH)

Following the procedure of Example 3, 1.27 g of crude VI

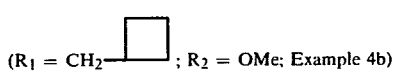
(R$_1$ = CH$_2$—☐; R$_2$ = OMe; Example 4b)

gave 0.67 g (after crystallization from isopropyl alcohol; 55% yield) of VI

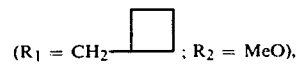
(R$_1$ = CH$_2$—☐; R$_2$ = MeO).

mp 177°–178°. Mass spectrum: m/e calcd. 313.2040; found 313.2017.

Anal. Calcd. for C$_{20}$H$_{27}$NO$_2$: C, 76.64; H, 8.68 N, 4.47; Found: C, 76.89; H, 8.40; N, 4.38.

EXAMPLE 8

Alternate Synthesis of II (R$_1$=H; R$_2$=OMe)

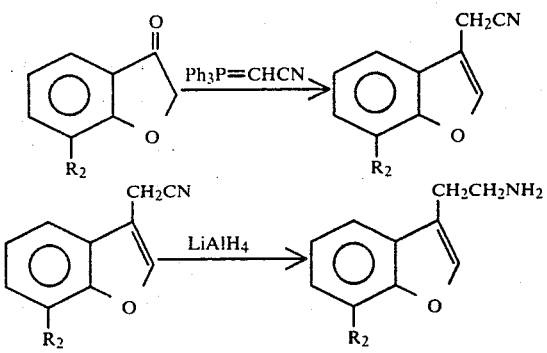

7-Methoxy-3-benzofuranethylamine

A mixture of 14.16 g of 7-methoxy-3-benzofuranone, 39.4 g of cyanomethylenetriphenylphosphorane and 70 ml of p-xylene was heated at reflux under nitrogen for 16 hours. The solvent was removed, the solid washed repeatedly with ether and the product obtained on removal of the solvent from the ether washings sublimed (145° bath, 1 micron). Crystallization of the sublimate from 20 ml of isopropyl alcohol gave 11.06 g (69% yield) of 7-methoxy-3-benzofuranacetonitrile. Nmr spectrum (in CDCl$_3$): τ2.4 (t, J=1–2 Hz, 1); 2.8–3.3 (m, 3); 6.0 (s, 3) and 6.3 (d, J=1–2 Hz, 2).

7-Methoxy-3-benzofuranacetonitrile (10.73 g) was placed in the thimble of a Soxhlet extractor, and the solid extracted into a mechanically stirred mixture of 3.1 g of lithium aluminum hydride and 150 ml of ether during two hrs. After an additional three hrs. at reflux the mixture was cooled and treated successively with 3.1 ml of water, 3.1 ml of 15% sodium hydroxide solution, and 9.3 ml of water. The mixture was filtered and the solid washed repeatedly with ether. The filtrate, on removal of the solvant, gave 10.16 g of product. It was dissolved in toluene and extracted with 2% hydrochloric acid. The extracts were made basic with aqueous sodium hydroxide solution and extracted with methylene chloride. Removal of the solvent and shortpath distillation of the residue (to 170° bath temperature, 1 micron) gave 4.33 g (39% yield) of 7-methoxy-3-benzofuranethylamine, identical with the product of Example 4a.

EXAMPLE 9

3-Cyclopropylmethyl-9-acetoxy-2,3,4,4aα,5,6,7,7aα-octahydro-1H-benzo[4,5]furo[3,2-e]isoquinoline

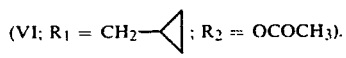
(VI; R$_1$ = CH$_2$—◁; R$_2$ = OCOCH$_3$).

A mixture of 1.13 g of VI

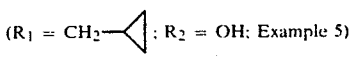
(R$_1$ = CH$_2$—◁; R$_2$ = OH; Example 5)

and 7 ml of acetic anhydride was heated under reflux for 40 minutes. Removal of the excess acetic anhydride and short-path distillation of the residue (180°–200° bath temperature; 0.1 micron pressure) gave VI ($R_1 = CH_2-$$; R_2 = OCOCH_3$)

as a viscous oil Nmr spectrum (220 MHz in CDCl$_3$): τ2.6 (d/d, J=7/1 Hz, 1); 3.0(d/d, J=8/1 Hz, 1); 3.2(m, 1); 5.5(t,J≃5.5 Hz,1) and 6.8–10.0(m,23). Mass spectrum: m/e calcd. 341.1989; Found: 341.1976.

EXAMPLE 10

3-Benzyl-9-methoxy-2,3,4,4aα,5,6,7,7aα-octahydro-1H-benzo[4,5]furo[3,2-e]isoquinoline (VI,R$_1$=CH$_2$Ph; R$_2$=OMe)

(a) N-Benzyl-7-methoxy-3-benzofuranethylamine (II, R$_1$=CH$_2$Ph; R$_2$=OMe) was prepared in 91% yield as described in Example 4b, substituting benzoyl chloride for cyclopropanecarbonyl chloride; it distilled at 180°–200° bath temperature under 0.5 micron pressure. Nmr spectrum (in CDCl$_3$) τ2.6(s,1); 2.7–3.4(m,8); 6.1(s,3); 6.3(s,3); 7.0–7.3(m,4) and 8.5(broad s,1).

(b) 3-Benzyl-9-methoxy-2,3-dihydro-1H-benzo[4,5]furo[3,2-e]isoquinolin-4[7aH]-one (IV, R$_1$=CH$_2$Ph; R$_2$=OMe)

N-Benzyl-7-methoxy-3-benzofuranethylamine (52.1 g) was treated with 6-α-pyronecarbonyl chloride as described in Example 1c and the resulting amide III (R$_1$=CH$_2$Ph, R$_2$=OMe) was heated under reflux with 12 liters of 1,2,4-trichlorobenzene in an atmosphere of nitrogen for 5 hours. Removal of the solvent and crystallization of the residue from ethyl acetate gave 26.55 g of 3-benzyl-9-methoxy-2,3-dihydro-1H-benzo[4,5]furo[3,2-e]isoquinoline-4[7aH]-one. Purification of the mother liquor by high-pressure liquid chromatography (silica gel, ethyl acetate-hexane 1:1) followed by crystallization from ethyl acetate gave another 7.99 g of product. Combined yield: 33.54 g (50%). An analytical sample had mp 135°–136°.

Anal. Calcd. for C$_{23}$H$_{21}$NO$_3$: C, 76.86; H, 5.89; N, 3.90. Found: C, 77.13; H, 5.98; N, 3.84.

(c) 3-Benzyl-9-methoxy-2,3,4,4aα,5,6,7,7aα-octahydro-1H-benzo[4,5]furo[3,2-e]isoquinoline (VI, R$_1$=CH$_2$Ph; R$_2$=OMe)

A mixture of 17.05 g of IV(R$_1$=CH$_2$Ph; R$_2$=OMe), 100 ml of tetrahydrofuran and 3 g of 10% palladium on charcoal was shaken under 48 psi initial hydrogen pressure at room temperature for 7 days. Removal of the solvent from the filtered solution gave 17.37 g of crude V (R$_1$=CH$_2$Ph; R$_2$=OMe). This was combined with the product from an identical hydrogenation and heated under reflux with 30 ml of borane-methyl sulfide and 200 ml of tetrahydrofuran under nitrogen overnight. The excess borane was decomposed with conc. hydrochloric acid, and the solvent was removed. The residue was made basic with 10% aqueous sodium carbonate solution and the product was extracted into methylene chloride. The residue obtained on removal of the solvent was heated under reflux with 100 ml of acetic acid and 30 ml of conc. hydrochloric acid for two hours. The mixture was concentrated and the residue was made basic with aqueous sodium carbonate solution and extracted with methylene chloride. Removal of the solvent from the dried extracts gave 30.91 g of 3-benzyl-9-methoxy-2,3,4,4aα,5,6,7,7aα-octahydro-1H-benzo[4,5]furo[3,2-e]isoquinoline. The product was converted to the hydrochloride salt which after crystallization from isopropyl alcohol melted at 169°–171°.

Anal. Calcd. for C$_{23}$H$_{28}$ClNO$_2$: C, 71.58; H, 7.31; N, 3.63, Found: C, 71.81; H, 7.39; N, 3.63.

EXAMPLE 11

3-Benzyl-2,3,4,4aα,5,6,7,7aα-octahydro-1H-benzo[4,5]furo[3,2-e]isoquinoline-9-ol (VI; R$_1$=CH$_2$Ph; R$_2$=OH)

Following the procedure of Example 5, VI (R$_1$=CH$_2$Ph; R$_2$=OMe) was converted to VI(R$_1$=CH$_2$Ph; R$_2$=OH), mp of the hydrochloride: 251°.

Anal. Calcd. for C$_{22}$H$_{26}$ClNO$_2$: C, 71.05; H, 7.05; N, 3.77. Found: C, 70.67; H, 7.08; N, 3.68.

EXAMPLE 12

9-Methoxy-2,3,4,4aα,5,6,7,7aα-octahydro-1H-benzo[4,5]furo[3,2-e]isoquinoline (VI, R$_1$=OMe)

A mixture of 26.8 g of the hydrochloride of VI(R$_1$=CH$_2$Ph; R$_2$=OMe; Example 10c), 100 ml of 90% aqueous ethanol and 2.5 g of 10% palladium on charcoal was shaken under 50 psi initial hydrogen pressure at room temperature until hydrogenolysis was complete. Removal of the solvent from the filtered solution and conversion of the hydrochloride so obtained to the free base with 10% aqueous sodium carbonate and methylene chloride gave 14.8 g of 9-methoxy-2,3,4,4aα,5,6,7,7aα-octahydro-1H-benzo[4,5]furo[3,2-e]isoquinoline (VI; R$_1$=H; R$_2$=OMe). Nmr spectrum (220 MHz in CDCl$_3$): τ2.6–2.8(m,1); 3.0–3.2(m,2); 5.5(t,J≃5.5 Hz,1); 6.1(s,3) and 6.5–9.0(m,14).

Mass spectrum: m/e calculated 259.1572; Found: 259.1580.

EXAMPLE 13

2,3,4,4aα,5,6,7,7aα-octahydro-1H-benzo[4,5]furo[3,2-e]isoquinolin-9-ol (VI, R$_1$=H; R$_2$=OH)

A mixture of 1.19 g of VI (R$_1$=H; R$_2$=OMe; Example 12), 1 g of potassium t-butoxide, 1 ml of n-propyl mercaptan and 20 ml of dimethyl formamide was stirred in an oil bath of 130° under nitrogen for 3 hours. Acetic acid (1 ml) was added to the cooled mixture, and the solvents were removed under vacuum. The residue was made basic with 10% aqueous sodium carbonate solution and the product was extracted into methylene chloride. Removal of the solvent from the dried extracts and crystallization of the residue from 90% aqueous ethanol gave 0.71 g of 9-hydroxy-2,3,4,4aα,5,6,7,7aα-octahydro-1H-benzo-[4,5]furo[3,2-e]isoquinoline-3-carboxyaldehyde, mp 208°–218°.

Anal. Calcd. for C$_{16}$H$_{19}$NO$_3$: C, 70.31; H, 7.01; N, 5.12. Found: C, 70.07; H, 7.06; N, 5.03.

The above product was heated under reflux with a 10:1 mixture of methanol and conc. hydrochloric acid for 4.5 hours. Removal of the solvent and crystallization of the residue from 90% aqueous ethanol gave the hydrochloride of 2,3,4,4aα,5,6,7,7aα-octahydro-1H-benzo[4,5]furo[3,2-e]isoquinolin-9-ol, mp >260°.

Anal. Calcd. for C$_{15}$H$_{20}$ClNO$_2$: C, 63.94; H, 7.15; N, 4.97. Found: C, 64.04; H, 7.17; N, 5.13.

EXAMPLE 14

3-Ethyl-2,3,4,4aα,5,6,7,7aα-octahydro-1H-benzo[4,5-]furo[3,2-e]isoquinolin-9-ol (VI, $R_1=C_2H_5$; $R_2=OH$)

(a) Acetyl chloride (1 ml) was added to a stirred mixture of 1.00 g of 9-methoxy-2,3,4,4aα-5,6,7,7aα-octahydro-1H-benzo[4,5]furo[3,2-e]isoquinoline (Example 12), 8 ml of methylene chloride, and 10 ml of 15% aqueous sodium hydroxide solution, keeping the temperature below 15°. The layers were separated after stirring at room temperature for 3 hours, and the aqueous phase was extracted once with methylene chloride. The combined methylene chloride layers were dried and concentrated to give 1.17 g of crude 3-acetyl-9-methoxy-2,3,4,4aα,5,6,7,7aα-octahydro-1H-benzo[4,5-]furo[3,2-e]isoquinoline. This was reduced with 0.4 g of lithium aluminum hydride in tetrahydrofuran at reflux for 6 hours and the product was short path distilled at 0.5 micron pressure (bath temperature 170°) to give 0.97 g of 3-ethyl-9-methoxy-2,3,4,4aα,5,6,7,7aα-octahydro-1H-benzo[4,5]furo[3,2-e]isoquinoline (VI, $R_1=C_2H_5$; $R_2=OMe$). Nmr spectrum (220 MHz, in $CDCl_3$): τ2.8–3.0(m,1); 3.2–3.3(m,2); 5.5(t,J≈5 Hz,1); 6.1(s,3); 7.0–8.6(m,15) and 8.8(t,J=7 Hz,3).

(b) A mixture of 0.84 g of VI(R=$C_2H_5$; $R_2=OMe$; above), 1 g of potassium t-butoxide, 1.3 ml of n-propyl mercaptan and 20 ml of dimethylformamide was stirred under nitrogen in an oil bath at 130° for 5 hours. The cooled mixture was treated with 1 ml of acetic acid, and the volatiles were removed under vacuum. The residue was treated with dilute hydrochloric acid and ether, and the aqueous acidic phase was made basic with 10% aqueous sodium carbonate solution. Extraction with methylene chloride furnished, after drying and removal of the solvent, 0.82 g of crude product which on crystallization from 90% aqueous ethanol gave 0.49 g of 3-ethyl-2,3,4,4aα,5,6,7,7aα-octahydro-1H-benzo[4,5-]furo[3,2-e]isoquinolin-9-ol (VI, $R_1=C_2H_5$; $R_2=OH$), mp 189°–190°.

Anal. Calcd. for $C_{17}H_{23}NO_2$: C, 74.69; H, 8.48; N, 5.12. Found: C, 74.68; H, 8.44; N, 5.03.

EXAMPLE 15

3-Allyl-9-methoxy-2,3,4,4aα,5,6,7,7aα-octahydro-1H-benzo[4,5]furo[3,2-e]isoquinoline (VI, $R_1=CH_2CH=CH_2$; $R_2=OMe$)

A mixture of 1.31 g of VI($R_1=H$; $R_2=OMe$), 3 g of sodium bicarbonate, 8 ml of dimethylformamide and 2 ml of allyl bromide was stirred at room temperature overnight. Methanol was added, the mixture was filtered, and the solid was washed twice with hot methanol. Removal of the solvents from the filtrate gave 2.62 g of crude quaternary bromide. This salt was heated with 15 ml of methanol and 6.7 g of trimethylamine in a sealed tube to 100° for 8 hours. The solvent was removed and the residue was stirred with methylene chloride and 15% aqueous sodium hydroxide solution. Removal of the solvent from the dried methylene chloride solution and short-path distillation (140°–165° bath temperature, 0.05 microns pressure) gave 1.09 g of VI($R_1=CH_2CH=CH_2$; $R_2=OMe$). Nmr spectrum (220 MHz in $CDCl_3$): τ2.7–2.9(m,1); 3.1–3.2 (m,2); 3.7–4.3(m,1); 4.5–4.9(m,2); 5.5(t,J≈5.5 Hz,1); 6.1(s,3); 6.8(d, split further, 2), and 7.0–9.9(m,13).

EXAMPLE 16

3-Allyl-2,3,4,4aα,5,6,7,7aα-octahydro-1H-benzo[4,5-]furo[3,2-e]isoquinolin-9-ol (VI; $R_1=CH_2CH=CH_2$; $R_2=OH$)

Treatment of the quaternary salt obtained in Example 15 with potassium t-butoxide and n-propyl mercaptan in dimethyl formamide as described in Example 5 gave VI($R_1=CH_2CH=CH_2$; $R_2=H$), mp 160°–161°.

Anal. Calcd. for $C_{18}H_{23}NO_2$: C, 75.76; H, 8.12; N, 4.91. Found: C, 75.73; H, 8.00; N, 4.69.

EXAMPLE 17

3-(3'-Methyl-2'-butenyl)-9-methoxy-2,3,4,4aα,5,6,7,7aα-octahydro-1H-benzo[4,5]furo[3,2-e]isoquinoline(VI, $R_1=CH_2CH=CMe_2$; $R_2=OMe$)

Following the procedure of Example 15, but using 1-bromo-3-methyl-2-butene in place of allyl bromide gave VI($R_1=CH_2CH=CMe_2$; $R_2=OMe$) Nmr spectrum (220 MHz in $CDCl_3$): 2.8–3.0(m,1); 3.2–3.3(m,2); 4.7(t,J=7 Hz, split further, 1); 5.5(t, J≈5.5 Hz,1); 6.1(s,3); 7.0(d, split further, 2) and 7.1–9.1(m,19).

EXAMPLE 18

3-(3'-methyl-2'-butenyl)-2,3,4,4aα,5,6,7,7aα-octahydro-1H-benzo[4,5]furo[3,2-e]isoquinolin-9-ol(VI; $R_1=CH_2CH=CME_2$; $R_2=OH$)

Following the procedure of Example 16, but using the quaternary ammonium salt obtained in Example 17, there was obtained VI($R_1=CH_2CH=CMe_2$; $R_2=H$), mp 143°–144°.

Anal. Calcd. for $C_{20}H_{27}NO_2$: C, 76.64; H, 8.68; N, 4.47. Found: C, 76.62; H, 8.48; N, 4.28.

EXAMPLE 19

3-(3'-Methylbutyl)-2,3,4,4aα,5,6,7,7aα-octahydro-1H-benzo[4,5]furo[3,2-e]isoquinolin-9ol(VI; $R_1=CH_2CH_2CHMe_2$; $R_2=OH$)

Catalytic hydrogenation (tetrahydrofuran, prereduced platinum oxide) of VI($R_1=CH_2CH=CMe_2$; $R_2=OH$; Example 18) gave VI($R_1=CH_2CH_2CHMe_2$; $R_2=OH$), mp 188°–189°.

Anal. Calcd. for $C_{20}H_{29}NO_2$: C, 76.15; H, 9.27; N, 4.44. Found: C, 76.08; H, 8.97; N, 4.35.

EXAMPLE 20

9-Methoxy-2,3,4,4aα,5,6,7,7aα-octahydro-1H-benzo[4,5]furo[3,2-e]isoquinoline-3-acetonitrile (VI, $R_1=CH_2CN$; $R_2=OMe$).

A mixture of 1.32 g of VI($R_1=H$; $R_2=OMe$), 8 ml of dimethylformamide, 2.4 g of potassium carbonate and 2 ml of chloroacetonitrile was stirred at room temperature for 3.5 hours. The solvent was removed and the residue was stirred with toluene. Removal of the solvent from the filtered solution and crystallization from ethyl acetate gave 1.03 g of VI($R_1=CH_2CN$; $R_2=OMe$), mp 135°–136°.

Anal. Calcd. for $C_{18}H_{22}N_2O_2$: C, 72.46; H, 7.43; N, 9.39. Found: C, 72.26; H, 7.35; N, 9.20.

The following compounds were prepared from 9-methoxy-2,3,4,4aα,5,6,7,7aα-octahydro-1H-benzo[4,5-]furo[3,2-e]isoquinoline (VI; $R_1=H$; $R_2=OMe$) according to the procedures given in Example 14.

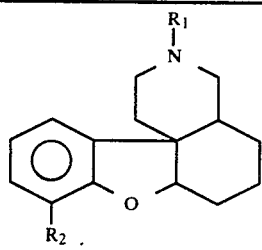

| Ex. No. | $R_1$ | $R_2$ | M p | Analytical Data |
|---|---|---|---|---|
| 21 | —(CH$_2$)$_2$Me | —OMe | oil | Nmr spectrum (220MHz in CDCl$_3$): τ 2.7–2.9(m,1); 3.0–3.2(m,2); 5.5(t, J≃5.5Hz,1); 6.1(s,3); 6.9–8.9(m,17); 9.0(t, J = 7Hz,3). |
| 22 | —(CH$_2$)$_2$Me | —OH | 146–148° | Anal. Calcd. for C$_{18}$H$_{25}$NO$_2$: C,75.22; H, 8.77; N, 4.87. Found: C, 75.29; H, 8.67; N, 4.80 |
| 23 | —(CH$_2$)$_3$Me | —OMe | oil | Nmr-spectrum (220 MHz in CDCl$_3$): τ 2.8–3.0(m,1); 3.1–3.3(m,2); 5.5(t, J≃5.5Hz,1); 6.1(s,3); 7.1–8.9(m,19) and 9.0(t, J = 7Hz,3). |
| 24 | —(CH$_2$)$_3$Me | —OH | 145–146° | Anal. Calcd. for C$_{19}$H$_{27}$NO$_2$: C, 75.71; H, 9.03; N, 4.65. Found: C, 76.01; H, 8.93; N, 4.61. |
| 25 | —(CH$_2$)$_4$Me | —OMe | oil | Nmr spectrum (220 MHz, in CDCl$_3$) τ 2.8–3.0(m,1); 3.1–3.3(m,2); 5.5(t, J≃5.5Hz,1); 6.1(s,3); 7.0–8.9(m,21) and 9.0 (t,J = 7Hz,3) |
| 26 | —(CH$_2$)$_4$Me | —OH | 220°(dec.; HCl salt) | Mass spectrum(free base): m/e calcd. 315.2197; Found 315.2189 |
| 27 | —(CH$_2$)$_5$Me | —OMe | oil | NMr spectrum (220MHz in CDCl$_3$) τ2.7–2.9(m,1); 3.1–3.3(m,2); 5.5(t, J≃5.5Hz,1); 6.1(s,3); 7.0–8.8(m,23) and 9.0(t, split further,3). |
| 28 | —(CH$_2$)$_5$Me | —OH | 218° (HCl salt) | Anal. (HCl salt) Calcd. for C$_{21}$H$_{32}$ClNO$_2$: C, 68.93; H, 8.81; N, 3.83. Found: C, 69.06; H, 8.49; N, 3.85. |
| 29 | —(CH$_2$)$_7$Me | —OMe | oil | Nmr spectrum (220 MHz in CDCl$_3$) τ2.8–3.0(m,1); 3.2–3.3(m,2); 5.5(t, J≃5.5Hz,1); 6.1(s,3); 7.0–8.8(m,27) and 9.1(t, split further,3). |
| 30 | —(CH$_2$)$_7$Me | —OH | 188–190° (hydrochloride) | Mass spectrum(free base); m/e calcd. 357.2666; Found: 357.2653. |
| 31 | —CH$_2$CHMe$_2$ | —OMe | oil | Nmr spectrum (220MHz in CDCl$_3$) τ2.8–3.0(m,1); 3.2–3.3(m,2); 5.5(t, J≃5.5Hz,1); 6.1(s,3); 7.1–8.8(m,16) and 9.1 (d,J = 7Hz,6) |
| 32 | —CH$_2$CHMe$_2$ | —OH | 170–171° | Anal. Calcd. for C$_{19}$H$_{27}$NO: C, 75.71; H, 9.03; N, 4.65. Found: C, 75.68; H, 8.90; N, 4.62. |
| 33 | —CH$_2$—⬡ | —OMe | oil | Nmr spectrum (220 MHz, in CDCl$_3$)τ2.8–3.0(m,1); 3.2–3.3(m,2); 5.6(t, J≃5.5Hz,1); 6.1(s,3); 7.0–9.5(m,26). |
| 34 | —CH$_2$—⬡ | —OH | 141–142° | Anal. Calcd. for C$_{22}$H$_{31}$NO$_2$: C, 77.38; H, 9.15; N, 4.10. Found: C, 77.12; H, 8.87; N, 3.95. |

-continued

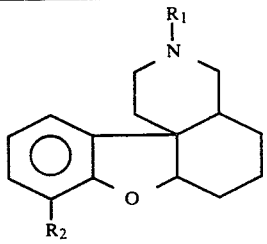

| Ex. No. | R₁ | R₂ | M p | Analytical Data |
|---|---|---|---|---|
| 35 | —(CH₂)₂—⟨C₆H₄⟩—Me | —OMe | >260° (HCl salt) | Nmr spectrum (free base, 220 MHz in CDCl₃): τ 2.8–3.0(m,5); 3.2–3.3(m,2); 5.6(t,J≈5Hz,1); 6.2(s,3); 7.0–7.5(m,8); 7.7 (s,3) and 7.8–9.0(m,9). |
| 36 | —(CH₂)₂—⟨C₆H₄⟩—Me | —OH | 136–140° | Mass Spectrum calcd. m/e 363.2197: found m/e 363.2208. |
| 37 | —CH₂-furyl | —OMe | oil | Nmr spectrum(220 MHz, in CDCl₃): τ2.6(m,1); 3.0 (d/d, J = 6/3Hz,1); 3.2–3.2 (m,2); 3.7(m,1); 3.8(d, J = 3Hz,1); 5.5(t,J≈5Hz,1); 6.1(s,3); 6.3(s,2), and 7.1–9.0(13). |
| 38 | —CH₂-furyl | —OH | 135–137° | Anal. Calcd. for C₂₀H₂₃NO₃: C, 73.82; H, 7.23; N, 4.30. Found: C, 73.75; H, 7.18; N, 4.33. |
| 39 | —CH₂-tetrahydrofuryl | —OMe | oil | Nmr spectrum (220 MHz in CDCl₃): τ2.8–3.0(m,1); 3.2–3.3(m,2); 5.5(t,J≈5.5 Hz,1); 5.8–6.3(m + s,6); 7.0–7.5(m,6) and 7.9–9.0(m,13). |
| 40 | —CH₂-tetrahydrofuryl | —OH | 138–145° | Anal. Calcd. for C₂₀H₂₇NO₃: C, 72.92; H, 8.26; N, 4.25. Found: C; 72.87; H, 8.14; N, 4.40. |
| 41 | —CH₂-thienyl | —OMe | oil | Nmr spectrum (220 MHz in CDCl₃): τ2.7–2.9(m,1); 3.0–3.2(m,3); 3.3–3.4(m,2); 5.6(t,J≈5.5Hz,1); 6.2(2s, 5); 7.1–9.0(m,13). |
| 42 | —CH₂-thienyl | —OH | 126–128° | Mass spectrum: m/e calcd. 341.1448; Found: 341.1443. |

Description of compounds of this invention by variation in substituents

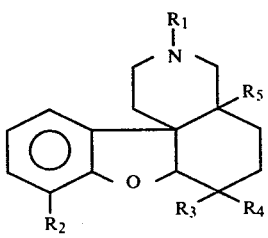

(1) Variation of R₁

(a) R₁=C₁₋₁₀ alkyl, —CH₂R₆ (R₆=C₃₋₆ cycloalkyl, tetrahydrofurylmethyl, tetrahydrofuryl), —C₂H₄—⟨C₆H₄⟩—R₇;

(R₇=C₁₋₃ alkyl, —OCH₃, —Cl, —Br, —F): by starting with the corresponding amines II which in turn are prepared from the amine II (R₁=H) by acylation followed by reduction as examplified in Example 4b or directly from the tosylate of I and R₁NH₂ as shown in Example 1b. Alternatively, these groups could be introduced into VI (R₁=H; R₂=H or alkoxy) by acylation followed by reduction or by direct alkylation.

Thus, substituting n-propylamine for methylamine in Example 2b there is obtained 7-methoxy-N-n-propyl-3-benzofuranethylamine, which by the procedures of Example 2c, 2d, and 3 is converted to 3-n-propyl-2,3,4,4a,-5,6,7,7a-octahydro-1H-benzo[4,5]furo[3,2-e]isoquinolin-9-ol (R₁=n-propyl; R₂=OH; R₃, R₄, R₅=H).

Substituting p-methylphenylacetyl chloride for cyclopropanecarbonyl chloride in Example 4b there is obtained N-p-methylphenethyl-7-methoxy-3-benzofuranethylamine which by the procedures of Examples 2c, 2d and 3 is converted to 3-p-methylphenethyl-2,3,4,4a,-5,6,7,7a-octahydro-1H-benzo[4,5]furo[3,2-e]isoquinolin-9ol

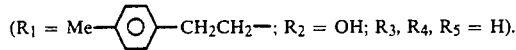

($R_1$ = Me—⟨O⟩—CH$_2$CH$_2$—; $R_2$ = OH; $R_3$, $R_4$, $R_5$ = H).

Treating 9-methoxy-2,3,4,4a,5,6,7,7a-octahydro-1H-benzo[4,5]furo[3,2-e]isoquinoline (VI, $R_1$=H; $R_2$=OMe) with tetrahydrofuroyl chloride in the presence of a base such as aqueous sodium hydroxide solution gives 9-methoxy-3-tetrahydrofuroyl-2,3,4,4a,5,6,7,7a-octahydro-1H-benzo[4,5]furo[3,2-e]isoquinoline, which on reduction with lithium aluminum hydride affords 9-methoxy-3-tetrahydrofurylmethyl-2,3,4,4a,5,6,7,7a-octahydro-1H-benzo[4,5]furo[3,2-e]isoquinoline

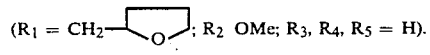

($R_1$ = CH$_2$—⟨O⟩; $R_2$ OMe; $R_3$, $R_4$, $R_5$ = H).

Similarly, 3-p-chlorophenethyl-2,3,4,4a,5,6,7,7a-octahydro-1H-benzo[4,5]furo[3,2-e]isoquinolin-9-ol is produced using p-chlorophenylacetyl chloride.

Treating 9-ethoxy-2,3,4,4a,5,6,7,7a-octahydro-1H-benzo[4,5]furo[3,2-e]isoquinoline with cyclohexylmethyl bromide in the presence of a base such as potassium carbonate in a solvent such as dimethylformamide gives 3-cyclohexylmethyl-9-ethoxy-2,3,4,4a,5,6,7,7a-octahydro-1H-benzo[4,5]furo[3,2-e]isoquinoline

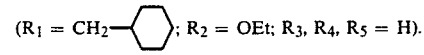

($R_1$ = CH$_2$—⟨ ⟩; $R_2$ = OEt; $R_3$, $R_4$, $R_5$ = H).

(b) $R_1$=H: by demethylation of the corresponding 3-methyl compound ($R_1$=Me) by any standard method such as treatment with cyanogen bromide or phenyl chloroformate or by catalytic hydrogenolysis of the 3-benzyl derivative ($R_1$=CH$_2$Ph) prepared as described in (1a) above.

Thus, 9-methoxy-3-methyl-2,3,4,4a,5,6,7,7a-octahydro-1H-benzo[4,5]furo[3,2-e]isoquinoline (Example 2d) is heated to reflux with cyanogen bromide in methylene chloride and the crude product is then heated with potassium hydroxide in ethylene glycol to 170° to give 9-methoxy-2,3,4,4a,5,6,7,7a-octahydro-1H-benzo[4,5-]furo[3,2-e]isoquinoline ($R_1$=H; $R_2$=OMe; $R_3$, $R_4$, $R_5$=H).

3-Benzyl-9-ethoxy-2,3,4,4a,5,6,7,7a-octahydro-1H-benzo[4,5]furo[3,2-e]isoquinoline on stirring in acetic acid or ethanol solution, optionally in the presence of hydrochloric acid, with a catalyst such as palladium on charcoal under an atmosphere of hydrogen gives, after workup, 9-ethoxy-2,3,4,4a,5,6,7,7a-octahydro-1H-benzo[4,5]furo[3,2-e]isoquinoline ($R_1$=H; $R_2$=OEt; $R_3$, $R_4$, $R_5$=H).

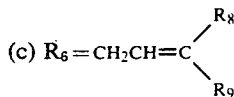

(c) $R_6$ = CH$_2$CH=C⟨$R_8$/$R_9$

C≡CH, 2-thienyl, 2-furyl. These groups are introduced after the intramolecular Diels-Alder reaction since they interfere with that reaction. The secondary amines VI ($R_1$=H) are alkylated with

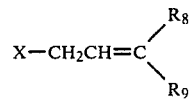

X—CH$_2$CH=C⟨$R_8$/$R_9$ (X=Cl, Br or I) or X—CH$_2$C≡CH; any quaternary salt formed can be converted to tertiary amine by heating with trimethylamine in methanol. The 2-thienyl or 2-furyl is introduced by acylation of the secondary amines VI ($R_1$=H) with

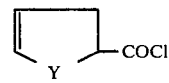

(Y=O or S) followed by reduction with LiAlH$_4$.

Thus, 9-methoxy-2,3,4,4a,5,6,7,7a-octahydro-1H-benzo[4,5]furo[3,2-e]isoquinoline, when treated with allyl bromide in the presence of a base such as potassium carbonate, gives 3-allyl-9-methoxy-2,3,4,4a,5,6,7,7a-octahydro-1H-benzo[4,5]furo[3,2-e]isoquinoline ($R_1$=CH$_2$CH=CH$_2$; $R_2$=MeO; $R_3$, $R_4$, $R_5$=H). Also, thienyl or furyl carbonyl chlorides followed by reduction with lithium aluminum hydride give 3-(2-thienyl-methyl or 2-furylmethyl-9-methoxy-2,3,4,4a,5,6,7,7a-octahydro-1H-benzo[4,5]furo[3,2-e]isoquinoline

(VI; $R_1$ = CH$_2$—⟨S⟩ or CH$_2$—⟨O⟩; $R_2$ = OMe).

(d) $R_1$=(CH$_2$)$_n$CN where n=1, 2 or 3 are prepared by alkylation of VI ($R_1$=H) with X(CH$_2$)$_n$CN where X=Cl, Br or I to give e.g., 3-β-cyanoethyl-9-methoxy-2,3,4,4a,5,6,7,7a-octahydro-1H-benzo[4,3]furo[3,2-e]isoquinoline (VI; $R_1$=CH$_2$CH$_2$CN; $R_2$=OMe).

(2) Variation of $R_2$

Introduction of $R_2$=H, OH, and OMe is exemplified in the examples; by starting with the appropriate benzofuran, $R_2$ can be OEt (i.e. C$_2$ alkoxy). Alternatively, the phenols VI ($R_2$=OH) may be alkylated, for instance with ethyl iodide and sodium hydride; C$_{2-12}$ acyloxy is introduced by acylating the phenols VI ($R_2$=OH) by standard methods.

Thus, substituting methyl-3-ethoxysalicylate for methyl o-vanillate in Example 2a there is obtained 7-ethoxy-3-benzofuranethanol. Further treatment according to the procedure of Examples 2b, 2c, and 2d gives 9-ethoxy-3-methyl-2,3,4,4a,5,6,7a-octahydro-1H-benzo[4,5]furo[3,2-e]isoquinoline ($R_1$=Me; $R_2$=OEt; $R_3$, $R_4$, $R_5$=H).

Treatment of 3-cyclopropylmethyl-2,3,4,4a,5,6,7,7a-octahydro-1H-benzo[4,5]furo[3,2-e]isoquinolin-9-ol (Example 5) with propionyl chloride in dimethylformamide in the presence of a base such as triethylamine or potassium carbonate gives the propionate ester of 3-cyclopropylmethyl-2,3,4,4a,5,6,7,7a-octahydro-1H-benzo[4,5]furo[3,2-e]isoquinolin-9-ol ($R_1 = CH_2-\triangleleft$; $R_2 = OCOCH_2CH_2CH_3$; $R_3$, $R_4$, $R_5$ = H).

(3) Variation of $R_3$ and $R_4$

Reaction of dienamides of type IV with singlet oxygen followed by treatment with base gives 4a-hydroxy-2,7a-dihydro-1H-benzo[4,5]furo[3,2-e]isoquinolin-4,7-(3,4aH)-dione (IX) which on treatment with

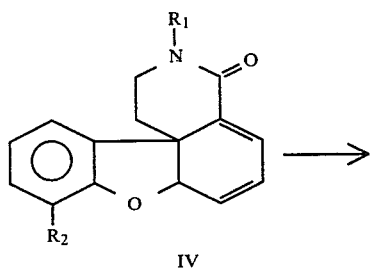

IV

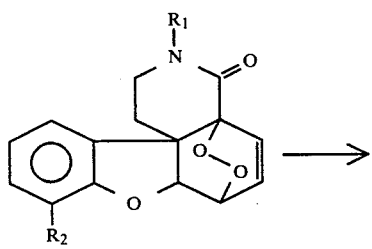

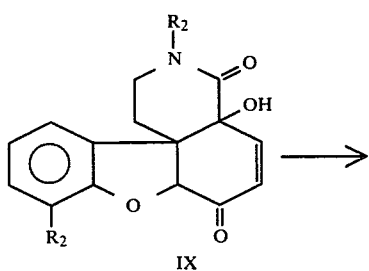

IX

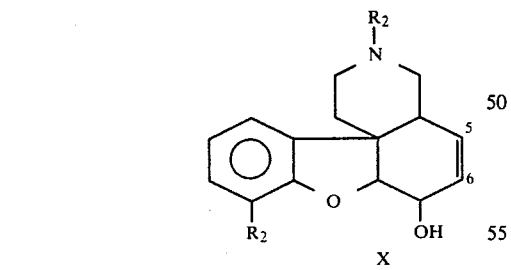

X methanesulfonyl chloride and a base, followed by reduction with a complex hydride such as lithium aluminum tri-tert-butoxy hydride gives the 2,3,4,4a,7,7a-hexahydro-1H-benzo[4,5]furo[3,2-e]isoquinolin-7-ols X. Saturation of the double bond in X gives 2,3,4,4a,5,6,7,7a-octahydro-1H-benzo[4,5]furo[3,2-e]isoquinolin-7-ols (XI). The preferred compounds have the 7β-hydroxy group as in morphine.

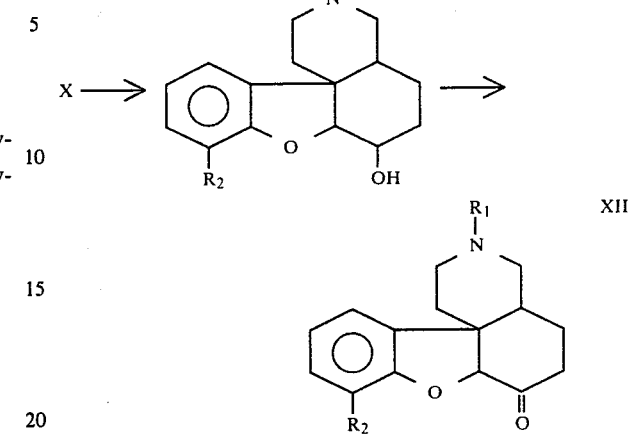

These can be alkylated or acylated to give compounds with $R_3$=alkoxy or acyloxy; treatment with diethylamino sulfur trifluoride gives the derivatives where $R_3$=F. Reaction of XI with p-toluenesulfonyl chloride in pyridine and treatment of the resulting tosylate with sodium azide in a polar solvent such as dimethyl sulfoxide gives the compounds where $R_3$=$N_3$. Oxidation of XI, for instance with Jones' reagent, gives 2,4,4a,5,6,7a-hexahydro-1H-benzo[4,5]furo[3,2-e]isoquinolin-7[3H]-ones (XII). Reaction of XII with methylene triphenylphosphorane followed by catalytic hydrogenation gives compounds where $R_3$=Me. The difluoro derivative ($R_3$, $R_4$=F) is obtained by treating XII with diethylaminosulfur trifluoride.

Catalytic hydrogenation of IX followed by reduction with a complex hydride

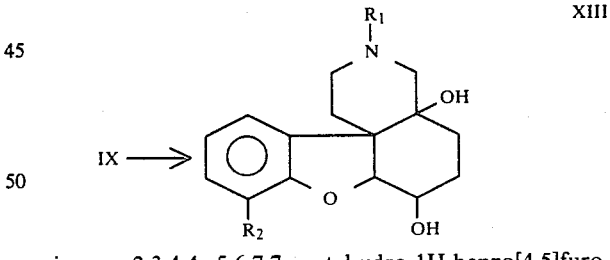

gives 2,3,4,4a,5,6,7,7a-octahydro-1H-benzo[4,5]furo-[3,2-e]isoquinolin-4a,7-diols (XIII).

Catalytic hydrogenation of the dieneamides IV can be stopped after the less hindered 6,7-double bond only has been saturated, giving 2,6,7,7a-tetrahydro-1H-benzo[4,5]furo[3,2-e]isoquinolin-4[3H]-ones (XIV). These on treatment with a peracid, such as m-chloroperbenzoic acid, give 4a,5-epoxy-2,4a,5,6,7,7a-hexahydro-1H-benzo[4,5]furo[3,2-e]isoquinolin-4[3H]-ones (XV) which on reduction with a metal hydride such as lithium aluminum hydride furnish the 2,3,4,4a,5,6,7,7a-octahydro-1H-benzo[4,5]furo[3,2-e]isoquinolin-4a-ols (XVI).

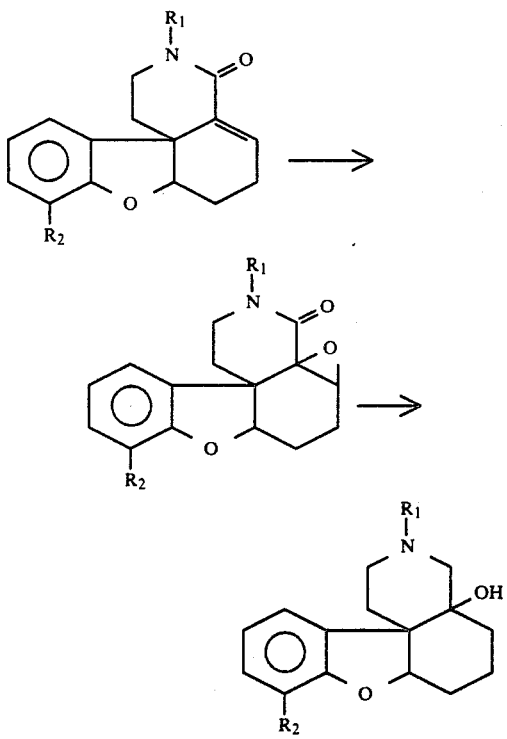

Thus, reaction of 3-cyclopropylmethyl-9-methoxy-2,3-dihydro-1H-benzo[4,5]furo[3,2-e]isoquinolin-4-[4aH]one (Example 4c) with singlet oxygen, generated for instance by reaction of hydrogen peroxide with sodium hypochlorite, followed by treatment with aqueous sodium hydroxide, gives 3-cyclopropylmethyl-4a-hydroxy-9-methoxy-2,7a-dihydro-1H-benzo[4,5-]furo[3,2-e]iso quinolin-4,7[3,4H]-dione (IX; $R_1$ = CH$_2$—◁ ; $R_2$ = MeO).

This, on treament with methanesulfonyl chloride in pyridine, followed by reduction with lithium aluminum tri-tert-butoxy hydride gives 3-cyclopropylmethyl-9-methoxy-2,3,4,4a,7,7a-hexahydro-1H-benzo[4,5-]furo[3,2-e]isoquinolin-7-ol (X; $R_1$ = CH$_2$—◁ $R_2$ = MeO).

Catalytic hydrogenation of this compound gives 3-cyclopropylmethyl-9-methoxy-2,3,4,4a,5,6,7,7a-octahydro-1H-benzo[4,5]furo[3,2-e]isoquinolin-7-ol

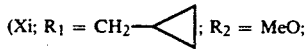

general formula; $R_1$ = CH$_2$—◁

Reaction of XI ($R_1$ = CH$_2$—◁ ; $R_2$ = OMe)

with sodium hydride and methyl iodide gives 3-cyclopropylmethyl-7,9-dimethoxy-2,3,4,4a,5,6,7,7a-octahydro-1H-benzo[4,5]furo[3,2-e]isoquinoline (general formula; $R_1$ = CH$_2$—◁ $R_2$, $R_3$ = OMe; $R_4$, $R_5$ = H).

Acylation of XI

XI ($R_1$ = CH$_2$—◁ ;$R_2$ = OMe)

with acetic anhydride and pyridine gives the acetate of 3-cyclopropylmethyl-9-methoxy-2,3,4,4a,5,6,7,7a-octahydro-1H-benzo[4,5]furo[3,2-e]isoquinolin-7-ol (general formula: $R_1$ = CH$_2$—◁ ;

$R_2$ = OMe; $R_3$ = OCOCH$_3$; $R_4$, $R_5$ = H).

Reaction of XI ($R_1$ = CH$_2$—◁ ; $R_2$ = OMe)

with diethylaminosulfur trifluoride gives 3-cyclopropylmethyl-7-fluoro-9-methoxy-2,3,4,4a,5,6,7,7a-octahydro-1H-benzo[4,5]furo[3,2-e]isoquinoline (general formula: $R_1$ = CH$_2$—◁ ;

$R_2$ = OMe; $R_3$ = F; $R_4$, $R_5$ = H).

Reaction of XI ($R_1$ = CH$_2$—◁ ; $R_2$ = OMe)

with p-toluenesulfonyl chloride in pyridine, followed by treatment of the tosylate with sodium azide in dimethylsulfoxide gives 3-cyclopropylmethyl-7-azido-9-methoxy-2,3,4,4a,5,6,7,7a-octahydro-1H-benzo[4,5-]furo[3,2-e]isoquinoline ($R_1$ = CH$_2$—◁ ; $R_2$ = OMe; $R_3$ = N$_3$; $R_4$, $R_5$ = H).

Oxidation of XI ($R_1$ = CH$_2$—◁ ; $R_2$ = OMe)

with chromium trioxide gives 3-cyclopropylmethyl-9-methoxy-2,4,4a,5,6,7-hexahydro-1H-benzo[4,5]furo[3,2-e]isoquinolin-7[3H]-one (XII, $R_1 = CH_2-\triangleleft$; $R_2 = $ OMe;

general formula $R_1 = CH_2-\triangleleft$;

$R_2 = $ OMe; $R_3$, $R_4$ combined $= $ O; $R_5 = $ H).

Reaction of this compound with methylenetriphenylphosphorane followed by catalytic hydrogenation of the resulting 7-methylene derivative gives 3-cyclopropylmethyl-9-methoxy-7-methyl-2,3,4,4a,5,6,7,7a-octahydro-1H-benzo[4,5]furo[3,2-e]isoquinoline (general formula: $R_1$ $CH_2-\triangleleft$;

$R_2 = $ OMe; $R_3 = $ Me; $R_4$, $R_5 = $ H).

Reaction of XII ($R_1 = CH_2-\triangleleft$; $R_2 = $ OMe)

with diethylaminosulfur trifluoride gives 3-cyclopropylmethyl-7,7-difluoro-9-methoxy-2,3,4,4a,5,6,7,7a-octahydro-1H-benzo[4,5]furo[3,2-e]isoquinoline (general formula: $R_1 = CH_2-\triangleleft$;

$R_2 = $ OMe; $R_3$, $R_4 = $ F; $R_5 = $ H).

Catalytic hydrogenation of IX ($R_1 = CH_2-\triangleleft$; $R_2 = $ OMe)

followed by reduction with lithium aluminum hydride gives 9-methoxy-2,3,4,4a,5,6,7,7a-octahydro-1H-benzo[4,5]furo[3,2-e]isoquinolin-4a,7-diol (XIII: $R_1 = CH_2-\triangleleft$; $R_2 = $ OMe;

general formula $R_1 = CH_2-\triangleleft$ $R_2 = $ OMe;

$R_3$, $R_5 = $ OH; $R_4 = $ H).

Catalytic hydrogenation of 3-cyclopropylmethyl 9-methoxy-2,3-dihydro-1H-benzo[4,5]furo[3,2-e]isoquinolin-4[4H]-one (Example 4c) is carried out as in Example 4d but the reaction is stopped after one mole equivalent of hydrogen has been taken up, giving 3-cyclopropylmethyl-9-methoxy-2,6,7,7a-tetrahydro-1H-benzo[4,5]furo[3,2-e]isoquinolin-4[3H]-one. This, on treatment with m-chloroperbenzoic acid gives 3-cyclopropylmethyl-4a,5-epoxy-9-methoxy-2,4a,5,6,7,7a-hexahydro-1H-benzo[4,5]furo[3,2-e]isoquinolin-4[3H]-one which is reduced with lithium aluminum hydride to 3-cyclopropylmethyl-9-methoxy-2,3,4,4a,5,6,7,7a-octahydro-1H-benzo[4,5]furo[3,2-e]isoquinolin-4a-ol.

Pharmaceutically suitable acid addition salts of the compounds of this invention promote water solubility and include those made with physiologically acceptable acids that are known in the art; such salts include hydrochloride, sulfate, nitrate, phosphate, citrate, tartrate, maleate and the like.

UTILITY

The compounds of this invention can be administered orally at doses of about 0.01–100 mg/kg or preferably 0.05–25 mg/kg or more preferably 0.10–10 mg/kg. The compounds also can be given parenterally. The useful daily human oral dose is expected to be in the range of 10–200 mg. A typical dosage form could be capsules or a compressed tablet containing 2.5 to 10 mg active ingredient administered 1–4 times daily.

Analgesic Testing Procedures

A standard procedure for detecting and comparing the analgesic activity of compounds in this series for which there is good correlation with human efficacy is the standard phenylquinone writhing test modified from Siegmund, et al., *Proc. Soc. Exp. Biol. Med.*, 95, 729 (1957). A test compound suspended in 1% methocel ® was given orally to fasted (17-21 hours) female white mice, 5-20 animals per double blind test. Aqueous (0.01% phenyl-p-benzoquinone) phenylquinone was injected intraperitoneally at 24 minutes later using 0.20 ml per mouse. Commencing at 30 minutes after the oral administration of the test compound, the mice were observed for 10 minutes for a characteristic stretching or writhing syndrome which is indicative of pain induced by phenylquinone. The effective analgesic dose for 50% of the mice ($ED_{50}$) was calculated by the moving average method of Thompson, W. R., *Bact. Rev.*, 11, 115–145 (1947).

Narcotic analgesics produce in mice an erection and arching of the tail (90° or more) which is referable to spinal cord stimulation. This Straub tail reaction is not produced by other analgesics, including the narcotic antagonists.

The method used was modified from Shemano, I., and Wendel, H., *Tox. Appl. Pharm.*, 6, 334–9 (1964). $CF_1S$ female mice (18–21 g), 10–20 mice per dose, were intubated with log scaled doses of analgesic in 1% aqueous methylcellulose. A positive Straub tail response was recorded if a tail was erected 90° or more for 5 seconds at any time within 24 minutes after dosing. A quantal Straub tail $ED_{50}$ was calculated by the moving average method [Thompson, W. R., *Bact. Rev.*, 11, 115–145 (1947)].

TABLE 1

| Ex. | R¹ | R² | Oral Anti-PQW | Oral Straub-Tail | Intraperitoneal (i.p.) or subcutaneous (S.C.) Anti-Straub Tail |
|---|---|---|---|---|---|
| 1 | Me | H | 14. | >81. | — |
| 2 | Me | OMe | 9.8 | >135. | 10.1 (i.p.) |
| 3 | Me | | 3.5 | 135. | 0.27 (s.c.) |
| 3 | Me (−) isomer | OH | 2.1 | >135 | 0.14 (s.c.) |
| 3 | Me (+)isomer | OH | 61 | >135 | 3.3 (s.c.) |
| 4 | CH₂—△ | OMe | 19.7 | >135. | 0.31 (i.p.) |
| 5 | CH₂—△ | OH | 0.75 | >81. | 0.006 (s.c.) |
| 7 | CH₂—◇ | OH | 81. | >81. | 0.64 (i.p.) |
| Morphine | | | 3.0 | 48. | — |
| Pentazocine | | | 56. | >135. | 4.0 (s.c.) |
| 9 | CH₂—△ | OCCH₃ (O=) | 0.75 | >135. | 0.005 (s.c.) |
| 10 | —CH₂—⟨O⟩ | OMe | 48. | >81. | 48. (s.c.) |
| 11 | —CH₂—⟨O⟩ | OH | 29. | >81. | 1.2 (s.c.) |
| 12 | H | OMe | 47. | >81. | — |
| 13 | H | OH | 15. | >135. | >27. (s.c.) |
| 14a | C₂H₅ | OMe | 63. | >135. | 0.71 (s.c.) |
| 14b | C₂H₅ | OH | 135. | >135. | 0.028 (s.c.) |
| 15 | CH₂CH=CH₂ | OMe | 62. | >135. | 0.30 (s.c.) |
| 16 | CH₂CH=CH₂ | OH | 81. | >81. | 0.03 (s.c.) |
| 17 | CH₂CH=CMe₂ | OMe | 18.7 | >135. | 7.8 (s.c.) |
| 18 | CH₂CH=CMe₂ | OH | 10.8 | 32. | >27. (s.c.) |
| 19 | CH₂CH₂CHMe₂ | OH | 33. | >135. | 0.64 (s.c.) |
| 20 | CH₂CN | OMe | 26 | >135 | 27 (s.c.) |
| 21 | C₃H₇ | OMe | 78. | >135. | 0.08 (s.c.) |
| 22 | C₃H₇ | OH | 112. | >135. | 0.008 (s.c.) |
| 23 | C₄H₉ | OMe | 33. | >135. | 0.82 (s.c.) |
| 24 | C₄H₉ | OH | 23. | >135. | 0.032 (s.c.) |
| 25 | C₅H₁₁ | OMe | 6.2 | 57. | >27. (s.c.) |
| 26 | C₅H₁₁ | OH | 5.3 | 37. | >27. (s.c.) |
| 27 | C₆H₁₃ | OMe | 7. | 25. | >27. (s.c.) |
| 28 | C₆H₁₃ | OH | 2.9 | 26. | — |
| 29 | C₈H₁₇ | OMe | 7.2 | — | >27. (s.c.) |
| 30 | C₈H₁₇ | OH | 4.2 | 54. | — |
| 31 | CH₂CHMe₂ | OMe | 94. | >135. | 0.24 (s.c.) |
| 32 | CH₂CHMe₂ | OH | 63. | >135. | 0.03 (s.c.) |
| 33 | CH₂—⟨S⟩ | OMe | 135. | >135. | — |
| 34 | CH₂—⟨S⟩ | OH | 23. | >135. | >27. (s.c.) |
| 35 | —CH₂CH₂—⟨O⟩—Me | OMe | 1.7 | 52. | 56. (s.c.) |
| 36 | —CH₂CH₂—⟨O⟩—Me | OH | 0.67 | 39. | >81. (s.c.) |

TABLE 1-continued

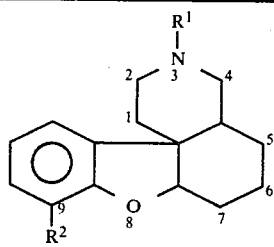

| Ex. | R[1] | R[2] | Oral Anti-PQW | Oral Straub-Tail | Intraperitoneal (i.p.) or subcutaneous (S.C.) Anti-Straub Tail |
|---|---|---|---|---|---|
| 37 | CH$_2$—furan | OMe | 84. | >135. | 12. (s.c.) |
| 38 | —CH$_2$—furan | OH | 108. | >135. | 7.2 (s.c.) |
| 39 | CH$_2$—tetrahydropyran | OCH$_3$ | 16.7 | — | 4.7 (s.c.) |
| 40 | CH$_2$—tetrahydropyran | OH | 11.8 | — | 0.19 (s.c.) |
| 41 | CH$_2$—thiophene | OMe | 48. | >135. | >27. (s.c.) |
| 42 | CH$_2$—thiophene | OH | 108. | >135. | — |

Known narcotic antagonists such as naloxone and nalorphine prevent the induction of Straub tail in mice by a highly addicting agonist such as morphine [H. Blumberg, H. B. Dayton and P. S. Wolf, *The Pharmacologist*, 10, 189 (1968)]. This property is the basis of a mouse test for narcotic antagonists.

Female CF$_1$S mice (fasted 17–21 hrs.), 5 per dose, were injected orally or subcutaneously with test drug at 0.67, 2, 6, 18, 54 and 162 mg/kg or other appropriate doses in 0.20 ml 1% Methocel ® per mouse. Five minutes later, 30 mg/kg of morphine sulfate in 0.20 ml 1% Methocel ® per mouse was given intraperitoneally starting ten minutes later, the mice were observed continuously for 5 minutes for evidence of Straub tail. Prevention of a 90° Straub tail during this observation period was taken as indication of narcotic antagonist ability.

The data are in Table 1. Most of the compounds were analgetic in the mouse antiphenylquinone test system and only a few caused Straub tail. Most also were antagonists in the mouse anti-Straub tail test.

The foregoing analgesia data show that most of the compounds of the invention are more potent than pentazocine and, indeed, compound of Example 5 is shown to have several times greater potency than morphine, which is the standard to which strong analgesics are compared. On the other hand, the very high Straub tail ED$_{50}$'s indicate that most of the compounds of the invention have very low likelihood of being addictive. In addition, the results of the Straub tail antagonism test show that most of the compounds of the invention have very high narcotic antagonism capability. Thus, the compounds of the invention are characterized by rapid onset of action, high oral potency and the ability to alleviate deepseated pain. Furthermore, abuse liability for most of the compounds should be extremely low or non-existent. In addition, some compounds of the invention which are pure narcotic antagonists, e.g., Example 10 will be useful for treatment of narcotic overdose.

DOSAGE FORMULATIONS

Analgesic and narcotic antagonistic agents of this invention can be administered to treat pain by any means that produces contact of the active agent with the agent's site of action in the body of a mammal. The compounds of the invention also can be used to alleviate the effect of narcotic agents. They can be administered by any conventional means available for use in conjunction with pharmaceuticals; either as individual therapeutic agents or in a combination of therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequent of treatment, and the effect desired. Usually a daily dosage of active ingredient can be about 0.01 to 100 milligrams per kilogram of body weight. Ordinarily 0.05 to 25 and preferably 0.10 to 10 milligrams per kilogram per day given in divided doses 1 to 4 times a day or in sustained release form is effective to obtain desired results.

Dosage forms (compositions) suitable for internal administration contain from about 0.1 milligram to about 500 milligrams of active ingredient per unit. In these pharmaceutical compositions the active ingredient will ordinarily be present in an amount of about 0.5–95% by weight based on the total weight of the composition.

The active ingredient can be administered orally in solid dosage forms, such as capsules, tablets, and powders, or in liquid dosage forms, such as elixirs, syrups, and suspensions; it can also be administered parenterally, in sterile liquid dosage forms.

Gelatin capsules contain the active ingredient and powdered carriers, such as lactose, sucrose, mannitol, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film-coated to mask any unpleasant taste and protect the tablet from the atmosphere, or enteric-coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration contain preferably a water soluble salt of the active ingredient, suitable stabilizing agents, and if necessary, buffer substances. Antioxidizing agents such as sodium bisulfite, sodium sulfite, or ascorbic acid either alone or combined are suitable stabilizing agents. Also used are citric acid and its salts and sodium EDTA. In addition, parenteral solutions can contain preservatives, such as benzalkonium chloride, methyl- or propyl-paraben, and chlorobutanol.

Suitable pharmaceutical carriers are described in *Remington's Pharmaceutical Sciences*, E. W. Martin, a standard reference text in this field.

Useful pharmaceutical dosage-forms for administration of the compounds of this invention can be illustrated as follows:

Capsules

A large number of unit capsules are prepared by filling standard two-piece hard gelatin capsules each with 10 milligrams of powdered active ingredient, 215 milligrams of lactose, 24 milligrams of talc, and 6 milligrams magnesium stearate.

Capsules

A mixture of active ingredient in soybean oil is prepared and injected by means of a positive displacement pump into gelatin to form soft gelatin capsules containing 10 milligrams of the active ingredient. The capsules are washed in petroleum ether and dried.

Tablets

A large number of tablets are prepared by conventional procedures so that the dosage unit is 10 milligrams of active ingredient, 6 milligrams of magnesium stearate, 70 milligrams of microcrystalline cellulose, 11 milligrams of cornstarch and 315 milligrams of lactose. Appropriate coatings may be applied to increase palatability or delay absorption.

Injectable

A parenteral composition suitable for administration by injection is prepared by stirring 2.0% by weight of active ingredient in 10% by volume propylene glycol and water. The solution is sterilized by filtration.

Suspension

An aqueous suspension is prepared for oral administration so that each 5 milliliters contain 2 milligrams of finely divided active ingredient, 200 milligrams of sodium carboxymethyl cellulose, 5 milligrams of sodium benzoate, 1.0 gram of sorbitol solution, U.S.P., and 0.025 milliliter of vanillin.

What is claimed is:

1. A compound of the formula

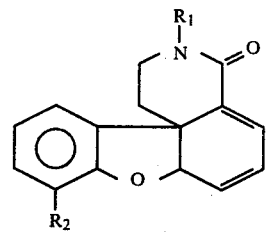

$R_1$ is selected from the group consisting of —H, $C_{1-10}$ alkyl, —CH$_2$—R$_6$,

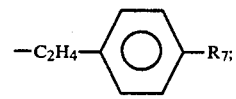

and (CH$_2$)$_n$CN in which n = 1–3;

$R_2$ is selected from the group consisting of H, —OH, $C_{1-2}$ alkoxy and $C_{2-12}$ acyloxy of an alkanoic acid;

$R_6$ is selected from the group consisting of

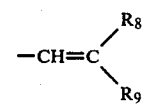

—C≡CH, $C_{3-6}$ cycloalkyl, 2-thienyl, 2-furyl and 2-tetrahydrofuryl, the 2-furyl and 2-tetrahydrofuryl optionally substituted with a methyl group;

$R_7$ is selected from the group consisting of $C_{1-3}$ alkyl, —OCH$_3$, —Cl, —Br and —F.

2. A compound of claim 1 in which $R_1$ is cyclopropylmethyl or cyclobutylmethyl.

3. A compound of claim 1 in which $R_1$ is —CH$_2$—R$_6$, and $R_6$ is $C_{3-6}$ cycloalkyl.

4. A compound of claim 1 in which $R_2$ is —OH.

5. A compound of claim 1 in which $R_2$ is —OCH$_3$.

* * * * *